United States Patent
Han et al.

(10) Patent No.: US 8,309,779 B2
(45) Date of Patent: *Nov. 13, 2012

(54) ETHYLENE OLIGOMERIZATION CATALYST SYSTEMS HAVING ENHANCED SELECTIVITY

(75) Inventors: Taek Kyu Han, Daejeon (KR); Sung Seok Chae, Daejeon (KR); Sang Ook Kang, Seoul (KR); Kyung Ryang Wee, Yeosu-si (KR); Sung Kwan Kim, Gyeongsangnam-do (KR)

(73) Assignees: SK Innovation Co., Ltd., Seoul (KR); SK Global Chemical Co., Ltd., Seoul (KR)

( * ) Notice: Subject to any disclaimer, the term of this patent is extended or adjusted under 35 U.S.C. 154(b) by 161 days.

This patent is subject to a terminal disclaimer.

(21) Appl. No.: 12/733,156

(22) PCT Filed: Dec. 24, 2007

(86) PCT No.: PCT/KR2007/006797
§ 371 (c)(1),
(2), (4) Date: Feb. 4, 2010

(87) PCT Pub. No.: WO2009/022770
PCT Pub. Date: Feb. 19, 2009

(65) Prior Publication Data
US 2010/0145124 A1   Jun. 10, 2010

(30) Foreign Application Priority Data
Aug. 16, 2007 (KR) .................. 10-2007-0082457

(51) Int. Cl.
*C07C 2/32* (2006.01)
(52) U.S. Cl. ........ 585/513; 585/502; 585/510; 585/511; 585/512
(58) Field of Classification Search .......... 585/502, 585/510, 511, 512, 513, 520, 521, 522, 523; 502/102, 103, 117, 118, 121, 150, 162
See application file for complete search history.

(56) References Cited

U.S. PATENT DOCUMENTS

| | | | | |
|---|---|---|---|---|
| 5,968,866 A | * | 10/1999 | Wu ...................... | 502/155 |
| 6,037,500 A | * | 3/2000 | Zhang .................. | 568/12 |
| 6,207,868 B1 | * | 3/2001 | Zhang .................. | 568/814 |
| 7,273,959 B2 | * | 9/2007 | Drent et al. ............ | 585/514 |
| 2005/0113622 A1 | | 5/2005 | Drent et al. | |
| 2007/0185360 A1 | * | 8/2007 | Buchanan et al. ..... | 585/521 |
| 2008/0058486 A1 | * | 3/2008 | McCullough et al. .. | 526/161 |

FOREIGN PATENT DOCUMENTS

| | | |
|---|---|---|
| KR | 1020060002741 | 9/2006 |
| WO | WO0138270 | 5/2001 |
| WO | WO0183447 | 11/2001 |
| WO | WO0204119 | 1/2002 |
| WO | WO2004056479 | 7/2004 |
| WO | WO2005123633 | 12/2005 |
| WO | WO 2005123633 A1 * | 12/2005 |

OTHER PUBLICATIONS

Simpson, et al., "Linear Low Density Polyethylene" in Encyclopedia of Polymer Science and Technology, John Wiley & Sons, 2001, available on-line Oct. 22, 2001.*
International Search Report of International Application No. PCT/KR2007/006797 dated May 16, 2008.
Koide, Y. et al.; "Alumoxanes as cocatalysts in the palladium-catalyzed copolymerization of carbon monoxide and ethylene: genesis of a structure-activity relationship", Organometallics, 15(9), Apr. 30, 1996, Abstract.
Office Action dated May 3, 2012 issued by the Chinese Patent Office regarding CN 1867401A, corresponding to US2005113622A.

* cited by examiner

*Primary Examiner* — In Suk Bullock
*Assistant Examiner* — Bradley Etherton
(74) *Attorney, Agent, or Firm* — Abelman, Frayne & Schwab

(57) ABSTRACT

Disclosed herein is a catalyst system for selective oligomerization of ethylene, which comprises a P—C—C—P framework ligand, which is $(R^1)(R^2)P—(R^5)CHCH(R^6)—P(R^3)(R^4)$, and a chromium-based metal compound. Also disclosed is a method of greatly enhancing the activity and selectivity of oligomerization, such as trimerization or tetramerization, using a ligand having a specific steric arrangement structure.

16 Claims, No Drawings

ETHYLENE OLIGOMERIZATION CATALYST SYSTEMS HAVING ENHANCED SELECTIVITY

TECHNICAL FIELD

The present invention relates to a catalyst system for use in oligomerization, such as ethylene trimerization or tetramerization, and more particularly to a method of increasing the activity and selectivity of ethylene oligomerization using a catalyst system, which comprises a transition metal or a transition metal precursor, a promoter and a ligand having a specific stereoisomeric structure.

BACKGROUND ART 1-hexene and 1-octene are important commercial raw materials, which are widely used as monomers or comonomers in polymerization processes to produce linear low-density polyethylene, and are obtained by purifying products of ethylene oligomerization. However, ethylene oligomerization reactions conducted to date are inefficient in that 1-hexene and 1-octene are produced together with significant amounts of butene, higher oligomers and polyethylene. In such prior ethylene oligomerization technology, the yield of a desired product is limited, because a range of α-olefins is generally produced following a Schulze-Flory or Poisson product distribution.

Recently, studies focused on either producing 1-hexene by selectively trimerizing ethylene through transition metal catalysis or producing 1-octene by selectively tetramerizing ethylene have been conducted, and most known transition metal catalysts for use in ethylene trimerization or tetramerization are chromium-based catalysts.

International Patent Publication WO 02/04119 discloses a chromium-based catalyst for ethylene trimerization, which comprises a ligand of the formula $(R^1)(R^2)X—Y—X(R^3)(R^4)$, wherein X is phosphorus, arsenic or antimony, Y is a linking group such as $—N(R^5)—$, and at least one of $R^1$, $R^2$, $R^3$ and $R^4$ has a polar substituent or an electron donating substituent.

Another publication discloses the use of (o-ethylphenyl)$_2$PN(Me)P(o-ethylphenyl)$_2$, a ligand which shows no catalytic activity for 1-hexene under catalytic conditions and has no polar substituent in at least one of $R^1$, $R^2$, $R^3$ and $R^4$ (Antea Carter et al., Chem. Commun., 2002, p. 858-859).

Also, Korean Patent Laid-Open Publication No. 2006-0002741 discloses that excellent activity and selectivity of ethylene trimerization can be achieved in practice through the use of a PNP ligand containing a non-polar substituent at the ortho position of a phenyl ring attached to phosphorus, for example, (o-ethylphenyl)$_2$PN(Me)P(o-ethylphenyl)$_2$.

Meanwhile, International Patent Publication WO 04/056479 discloses enhancing selectivity in a process of producing 1-octene by tetramerizing ethylene using a chromium-based catalyst containing a PNP ligand having no substituent on a phenyl ring attached to phosphorus. In the patent publication, examples of a heteroatom ligand which is used in the catalyst for ethylene tetramerization include (phenyl)$_2$PN(isopropyl)P(phenyl)$_2$, etc.

This prior publication discloses that the chromium-based catalyst, containing a heteroatomic ligand having both nitrogen and phosphorus heteroatoms, without any polar substituents on the hydrocarbyl or heterohydrocarbyl groups on the phosphorus atom, can be used to selectively tetramerize ethylene to produce 1-octene, often in excess of 70 mass % selectivity.

However, the prior publications do not suggest a concrete example of a heteroatom-containing ligand structure, which can tetramerize ethylene at high selectivity to produce 1-octene or trimerize ethylene at high selectivity to produce 1-hexene. Also, these publications suggest only a PNP-type framework structure, such as $(R^1)(R^2)P—(R^5)N—P(R^3)(R^4)$, which is a ligand having a selectivity to 1-octene of about 70 mass %. Moreover, the possible substituents for heteroatomic ligands are also limited.

In addition, the prior PNP-type backbone ligands containing heteroatoms have problems in that their activity in reactions for producing 1-octene or 1-hexene changes over time, and the reaction rate is greatly reduced.

DISCLOSURE

Technical Problem

The applicant has conducted ethylene oligomerization experiments while variously changing not only the structure between atoms P and P, but also substituents $R^1$, $R^2$, $R^3$ and $R^4$ on the P atoms, in order to overcome the catalyst stability problems in the prior technologies. As a result, the applicant has found that, when the inventive chromium-based catalyst having a P—C—C—P framework ligand containing no nitrogen is used, 1-hexene or 1-octene can be produced by trimerizing or tetramerizing ethylene with high selectivity, and furthermore, the catalyst activity is stable enough over time that the reaction rate can be maintained constant. Also, the applicant has found that, when structures adjacent to carbon atoms between two phosphorus atoms in the inventive ligand having the P—C—C—P framework structure are three-dimensionally changed, the activity and selectivity of trimerization and tetramerization can be greatly enhanced. On the basis of these findings, the present invention has been completed.

That is, it is an object of the present invention to provide a transition metal catalyst system, which comprises a P—C—C—P ligand having a specific steric structure, and thus can increase the yield of 1-hexene or 1-octene by oligomerizing ethylene with high selectivity, and may have stable catalyst activity, to thus continuously maintain a constant reaction rate.

Technical Solution

To achieve the above object, the present invention provides a catalyst system for selective ethylene oligomerization, which comprises a transition metal or transition metal precursor, a promoter and a ligand, represented by any one of the following Formulas 1 to 4:

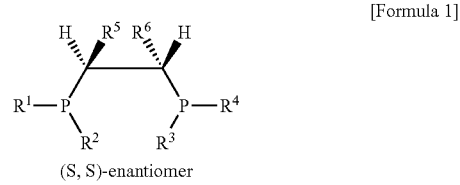

[Formula 1]

(S, S)-enantiomer

-continued

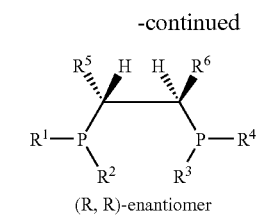

[Formula 2]

(R, R)-enantiomer

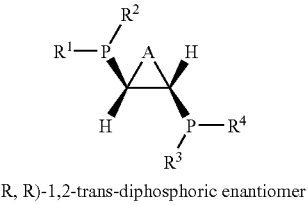

[Formula 3]

(R, R)-1,2-trans-diphosphoric enantiomer

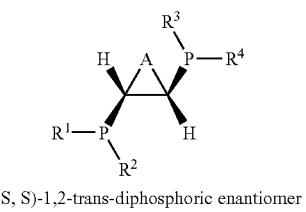

[Formula 4]

(S, S)-1,2-trans-diphosphoric enantiomer wherein $R^1$, $R^2$, $R^3$ and $R^4$ are each independently hydrocarbyl, substituted hydrocarbyl, heterohydrocarbyl or substituted heterohydrocarbyl, $R^5$ and $R^6$ are each independently hydrocarbyl or substituted hydrocarbyl, and A is hydrocarbyl, substituted hydrocarbyl, heterohydrocarbyl or substituted heterohydrocarbyl.

Advantageous Effects

According to the present invention, when ethylene oligomerization is performed using a chromium-based catalyst system, either comprising a linear ligand having an (S,S)- or (R,R)-isomeric P—C—C—P structure that is asymmetrical with respect to the symmetric plane, or comprising a trans cyclic ligand having a P—C—C—P structure of an (S,S)- or (R,R)-isomer, the activity and selectivity of trimerization or tetramerization can be significantly enhanced according to the arrangement direction and structure of substituents adjacent to the carbon atoms between the two phosphorus atoms, and thus 1-hexene or 1-ocetene can be produced with high selectivity.

BEST MODE

Hereinafter, the present invention will be described in further detail.

The present invention relates to a chromium-based catalyst system for selectively oligomerizing ethylene, which comprises a transition metal or a transition metal precursor, a promoter and a P—C—C—P framework ligand having stereospecificity. The inventive catalyst system can produce 1-hexene or 1-octene with high activity and high selectivity while maintaining stable reaction activity. According to the present invention, the activity and selectivity of trimerization and tetramerization can be greatly enhanced by sterically arranging structures adjacent to carbon atoms in two phosphorus atoms, particularly in the P—C—C—P framework compound, for use as a ligand.

As shown in Formulas 1, 2 and 5, in the structure of the PCH($R^5$)CH($R^6$)P ligand, three stereoisomers can exist, according to the directions in which substituents $R^5$ and $R^6$, adjacent to the respective carbon atoms, are bound to carbon. That is, each of the carbon atoms present in the P—C—C—P framework structure can be considered to be a chiral carbon atom, because the four substituents adjacent thereto are completely different, and in this case, two arrangement directions for each carbon can exist according to the direction in which substituents are attached to the carbon atoms. According to the arrangement direction of substituents, substituents on the respective chiral carbon atoms can be divided into (R) and (S) configurations by the Cahn-Ingold-Preg system.

In the framework structure of Formula 1, below, substituents on the first carbon are in the (S) configuration, because three substituents are arranged in an anti-clockwise direction according to the priority thereof, when the hydrogen substituent having the lowest priority is pointed away from the viewer. Also, it can be seen that substituents on the right carbon are in the (S) configuration, when the lowest-priority hydrogen is pointed away from the viewer. The structure of Formula 2, below, is seen to be an (R,R)-isomer, when it is observed in the same manner as above. The structure of Formula 5 below is in the (R,S) configuration and is a meso-isomer, because the two carbons are chiral. Likewise, in the cyclo structure of Formula 6 below, when two adjacent diphosphine compounds are in the (R,S)-configuration, the diphosphine compounds are positioned in the same direction, and are cis-isomers.

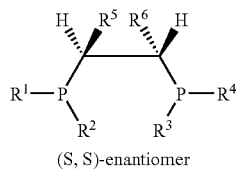

[Formula 1]

(S, S)-enantiomer

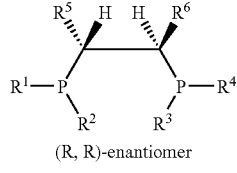

[Formula 2]

(R, R)-enantiomer

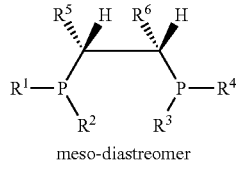

[Formula 5]

meso-diastreomer

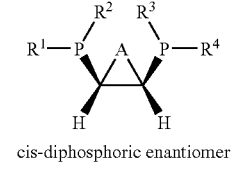

[Formula 6]

cis-diphosphoric enantiomer wherein $R^1$, $R^2$, $R^3$ and $R^4$ are each independently hydrocarbyl, substituted hydrocarbyl, heterohydrocarbyl or substituted heterohydrocarbyl, $R^5$ and $R^6$ are each independently hydrocarbyl or substituted hydrocarbyl, and A is hydrocarbyl, substituted hydrocarbyl, heterohydrocarbyl or substituted heterohydrocarbyl.

In the present invention, it was confirmed that chiral (S,S)- or (R,R)-isomers showed notably good selectivity and activity in ethylene trimerization or tetramerization compared to achiral meso-isomers. Likewise, it was observed that a ligand compound partially composed of an achiral trans-cyclic structure of P—C—C—P, as shown in Formulas 3 and 4, showed notably good selectivity and activity in ethylene trimerization or tetramerization compared to a chiral cis-cyclic structure.

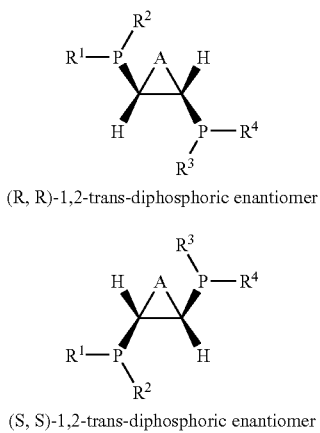

(R, R)-1,2-trans-diphosphoric enantiomer

[Formula 3]

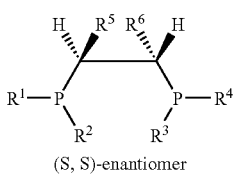

(S, S)-1,2-trans-diphosphoric enantiomer

[Formula 4]

wherein $R^1$, $R^2$, $R^3$ and $R^4$ are each independently hydrocarbyl, substituted hydrocarbyl, heterohydrocarbyl or substituted heterohydrocarbyl, and A is hydrocarbyl, substituted hydrocarbyl, heterohydrocarbyl or substituted heterohydrocarbyl.

That is, the present invention relates to a catalyst system comprising a P—C—C—P framework stereoisomeric compound, which has significantly increased selectivity and activity in ethylene oligomerization and, at the same time, maintains stable reaction activity, and more particularly to a catalyst system comprising a ligand having an achiral (S,S)- or (R,R)-isomeric P—C—C—P structure.

Hereinafter, the present invention will be described in further detail.

The catalyst system for selective oligomerization of ethylene according to the present invention comprises a transition metal or transition metal precursor, a promoter and a stereoisomeric ligand having a P—C—C—P framework structure, in which the catalyst system can have high activity and high selectively in ethylene oligomerization, and can maintain stable reaction activity. More particularly, the present invention relates to a catalyst system comprising a ligand having an (S,S)- or (R,R)-isomeric P—C—C—P structure that is sterically asymmetric with respect to the symmetric plane, as shown in the following Formulas 1 to 4:

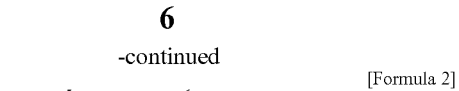

[Formula 1]

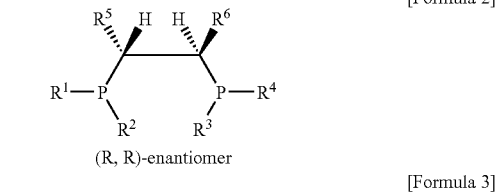

(S, S)-enantiomer

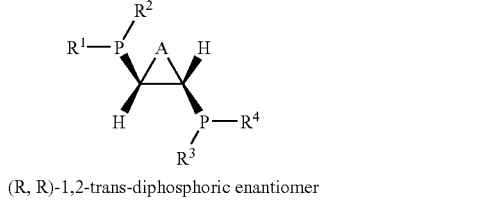

(R, R)-enantiomer

[Formula 2]

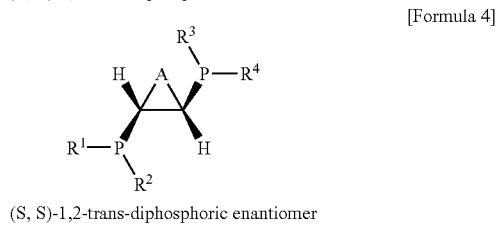

(R, R)-1,2-trans-diphosphoric enantiomer

[Formula 3]

[Formula 4]

wherein $R^1$, $R^2$, $R^3$ and $R^4$ are each independently hydrocarbyl, substituted hydrocarbyl, heterohydrocarbyl or substituted heterohydrocarbyl, and A is hydrocarbyl, substituted hydrocarbyl, heterohydrocarbyl or substituted heterohydrocarbyl.

In Formulas 1 to 4, suitable examples of $R^1$, $R^2$, $R^3$ and $R^4$ may include phenyl, benzyl, naphthyl, anthracenyl, mesityl, xenyl, methyl, ethyl, ethylenyl, propyl, propenyl, propinyl, butyl, cyclohexyl, 4-methylcyclohexyl, 4-ethylcyclohexyl, 4-isopropylcyclohexyl, tolyl, xylyl, 4-methylphenyl, 4-ethylphenyl, 4-isopropylphenyl, 4-t-butylphenyl, 4-methoxyphenyl, 4-isopropoxyphenyl, cumyl, methoxy, ethoxy, phenoxy, tolyloxy, dimethylamino, thiomethyl, trimethylsilyl, dimethylhydrazine, 2-methylcyclohexyl, 2-ethylcyclohexyl, 2-isopropylcyclohexyl, o-methylphenyl, o-ethylphenyl, o-isopropylphenyl, o-t-butylphenyl, o-methoxyphenyl, o-isopropoxyphenyl, biphenyl, naphthyl and anthracenyl, and may each be independently selected.

More preferably, $R^1$, $R^2$, $R^3$ and $R^4$ may each be independently selected from the group consisting of phenyl, tolyl, biphenyl, naphthyl, cyclohexyl, 4-methylphenyl, 4-ethylphenyl, 4-isopropylphenyl, 4-t-butylphenyl, 4-mehtoxyphenyl, 4-isopropoxyphenyl, 2-methylcyclohexyl, 2-ethylcyclohexyl, 2-isopropylcyclohexyl, o-methylphenyl, o-ethylphenyl, o-isopropylphenyl, o-t-butylphenyl, o-methoxyphenyl and o-isopropoxyphenyl.

$R^5$ and $R^6$ may each be independently selected from the group consisting of hydrocarbyl groups and substituted hydrocarbyl groups. More specifically, they may be selected from the group consisting of alkyl, aryloxy, halogen, nitro, alkoxycarbonyl, carbonyloxy, alkoxy, aminocarbonyl, carbonylamino, dialkylamino, derivatives thereof, and aryl substituted with any substituent.

The A group may be hydrocarbylene, substituted hydrocarbylene, heterohydrocarbylene or substituted heterohydrocarbylene, and more specifically, may be selected from the group consisting of $C_2$-$C_{10}$ alkylene, alkoxyene, alkoxycarbonyllene, carbonyloxy, aminocarbonylene, carbonylamino, alkylamino, and derivatives thereof.

In the ethylene oligomerization according to the present invention, the P—C—C—P framework ligand for stably maintaining selectivity to 1-hexene or 1-octene and reaction activity may be an (S,S)- or (R,R)-isomeric linear ligand or trans-cyclic ligand. Also, a mixture of two isomers, that is, a ligand consisting of a multiple bond of (S,S)- or (R,R)—($R^1$)($R^2$)P—($R^5$)CHCH($R^6$)—P($R^3$)($R^4$), may be used.

Examples of the stereoisomeric ligand constituting the P—C—C—P framework for maintaining activity, selectivity and stable activity in the selective oligomerization of ethylene according to the present invention include (S,S)- or (R,R)-(phenyl)$_2$P—CH(methyl)CH(methyl)-P(phenyl)$_2$, (S,S)- or (R,R)-(4-methoxyphenyl)$_2$P—CH(methyl)CH(methyl)-P(4-methoxyphenyl)$_2$, (S,S)- or (R,R)-(4-methylphenyl)$_2$P—CH(methyl)CH(methyl)-P(4-methylphenyl)$_2$, (S,S)- or (R,R)-(4-ethylphenyl)$_2$P—CH(methyl)CH(methyl)-P(phenyl)$_2$, (S,S)- or (R,R)-(4-ethylphenyl)$_2$P—CH(ethyl)CH(methyl)-P(4-ethylphenyl)$_2$, (S,S)- or (R,R)-(4-methoxyphenyl)$_2$P—CH(ethyl)CH(methyl)-P(phenyl)$_2$, (S,S)- or (R,R)-(4-ethylphenyl)$_2$P—CH(ethyl)CH(ethyl)-P(4-ethylphenyl)$_2$, (S,S)- or (R,R)-(phenyl)$_2$P—CH(ethyl)CH(ethyl)-P(phenyl)$_2$, (S,S)- or (R,R)-(phenyl)$_2$P—CH(isopropyl)CH(methyl)-P(phenyl)$_2$, (S,S)- or (R,R)-(4-methoxyphenyl)$_2$P—CH(isopropyl)CH(methyl)-P(4-methoxyphenyl)$_2$, (S,S)- or (R,R)-(4-ethylphenyl)$_2$P—CH(isopropyl)CH(methyl)-P(4-ethylphenyl)$_2$, (S,S)- or (R,R)-(phenyl)$_2$P—CH(n-propyl)CH(methyl)-P(phenyl)$_2$, (S,S)- or (R,R)-(4-methoxyphenyl)$_2$P—CH(n-propyl)CH(methyl)-P(4-methoxyphenyl)$_2$, (S,S)- or (R,R)-(4-ethylphenyl)$_2$P—CH(n-propyl)CH(methyl)-P(4-ethylphenyl)$_2$, (S,S)- or (R,R)-(phenyl)$_2$P—CH(isopropyl)CH(ethyl)-P(phenyl)$_2$, (S,S)- or (R,R)-(4-methoxyphenyl)$_2$P—CH(isopropyl)CH(ethyl)-P(4-methoxyphenyl)$_2$, (S,S)- or (R,R)-(4-ethylphenyl)$_2$P—CH(isopropyl)CH(ethyl)-P(4-ethylphenyl)$_2$, (S,S)- or (R,R)-trans-1,2-di-(P(phenyl)$_2$)cyclohexane, (S,S)- or (R,R)-trans-1,2-di-(P(4-methoxyphenyl)$_2$)cyclohexane, (S,S)- or (R,R)-trans-1,2-di-(P(4-ethylphenyl)$_2$)cyclohexane, (S,S)- or (R,R)-trans-1,2-di-(P(phenyl)$_2$)cyclopentane, (S,S)- or (R,R)-trans-1,2-di-(P(4-methoxyphenyl)$_2$)cyclopentane, (S,S)- or (R,R)-1,2-di-(P(4-ethylphenyl)$_2$)cyclopentane, (S,S)- or (R,R)-3,4-di-(P(phenyl)$_2$)pyrrole, (S,S)- or (R,R)-3,4-di-(P(4-methoxyphenyl)$_2$)pyrrole, (S,S)- or (R,R)-trans-3,4-di-(P(4-ethylphenyl)$_2$)pyrrole, (S,S)- or (R,R)-trans-3,4-di-(P(4-ethylphenyl)$_2$)imidazole, (S,S)- or (R,R)-(4-ethylphenyl)$_2$P—CH(dimethylamine)CH(dimethylamine)-P(4-ethylphenyl)$_2$, (S,S)- or (R,R)-(3-methoxyphenyl)$_2$P—CH(methyl)CH(methyl)-P(3-methoxyphenyl)$_2$, (S,S)- or (R,R)-(4-ethoxyphenyl)$_2$P—CH(methyl)CH(methyl)-P(o-ethoxyphenyl)$_2$, ((S,S)- or (R,R)-4-dimethylaminephenyl)$_2$P—CH(methyl)CH(methyl)P(4-dimethylaminephenyl)$_2$, (S,S)- or (R,R)-(4-ethylcyclohexyl)$_2$PCH(methyl)CH(methyl)P(4-ethylcyclohexyl)$_2$, (S,S)- or (R,R)-(2-ethylphenyl)$_2$PCH(methyl)CH(methyl)P(2-ethylphenyl)$_2$, (S,S)- or (R,R)-(2-isopropylphenyl)$_2$PCH(methyl)CH(methyl)P(2-isopropylphenyl)$_2$, (S,S)- or (R,R)-(2-methylphenyl)$_2$PCH(methyl)CH(methyl)P(2-methylphenyl)$_2$, (S,S)- or (R,R)-(2-ethylphenyl)$_2$PCH(methyl)CH(methyl)P(phenyl)$_2$, (S,S)- or (R,R)-(2-ethylphenyl)$_2$PCH(ethyl)CH(methyl)P(2-ethylphenyl)$_2$, (S,S)- or (R,R)-(2-ethylphenyl)$_2$PCH(ethyl)CH(ethyl)P(2-ethylphenyl)$_2$, (S,S)- or (R,R)-(2-ethylphenyl)$_2$PCH(isopropyl)CH(methyl)P(2-ethylphenyl)$_2$, (S,S)- or (R,R)-(2-ethylphenyl)$_2$PCH(n-propyl)CH(methyl)P(2-ethylphenyl)$_2$, (S,S)- or (R,R)-(2-ethylphenyl)$_2$PCH(isopropyl)CH(ethyl)P(2-ethylphenyl)$_2$, (S,S)- or (R,R)-trans-1,2-di-(P(2-ethylphenyl)$_2$)cyclohexane, (S,S)- or (R,R)-trans-1,2-di-(P(2-ethylphenyl)$_2$)cyclopentane, (S,S)- or (R,R)-trans-3,4-di-(P(2-ethylphenyl)$_2$)pyrrole, (S,S)- or (R,R)-trans-3,4-di-(P(2-ethylphenyl)$_2$)imidazole, (S,S)- or (R,R)-(2-ethylphenyl)$_2$PCH(dimethylamine)CH(dimethylamine)P(2-ethylphenyl)$_2$, (S,S)- or (R, R)-(2-methoxyphenyl)$_2$PCH(methyl)CH(methyl)P(2-methoxyphenyl)$_2$, (S,S)- or (R,R)-(2-ethoxyphenyl)$_2$PCH(methyl)CH(methyl)P(2-ethoxyphenyl)$_2$, (S,S)- or (R,R)-(2-dimethylaminephenyl)$_2$PCH(methyl)CH(methyl)P(2-dimethylaminephenyl)$_2$, (S,S)- or (R,R)-(2-ethylcyclohexyl)$_2$PCH(methyl)CH(methyl)P(2-ethylcyclohexyl)$_2$, (S,S)- or (R,R)-(phenyl)$_2$P—CH(phenyl)CH(phenyl)-P(phenyl)2, (1S,2S)- or (1R,2R)-trans-bis(diphenylphosphino)cyclohexane, and (1S,2S)- or (1R,2R)-trans-bis(di(4-methoxyphenyl)phosphino)cyclohexane but the scope of the present invention is not limited thereto, and the ligands according to the present invention can be prepared using various methods known to those skilled in the art.

The P—C—C—P-type stereoisomeric framework structure of the ligand according to the present invention is different from the prior (R)$_n$PN(R')P(R)$_m$ heteroligand, and the heteroatoms in the framework structure of the ligand according to the present invention are only phosphorus (P) atoms. That is, the ligand for use in the catalyst system according to the present invention comprises a carbon-carbon backbone structure without any nitrogen atom between the two phosphorus atoms. According to the present invention, the space structure of the ligand is suitably controlled in the arrangement direction of substituents attached to the carbon atoms, and thus the catalyst system according to the present invention can exhibit excellent catalytic activity, can achieve a 1-hexene selectivity or 1-octene selectivity higher than 70 wt %, and can maintain stable reaction activity.

For the highly selective production of hexene or octane, the catalyst system according to the ligand according to the present invention can be prepared through a method comprising a step of mixing a transition metal compound and an activating agent in any order.

The method for preparing the inventive catalyst system according to the present invention may comprise a step of producing a ligand coordination complex from a transition metal compound and the stereoisomeric ligand having the P—C—C—P framework structure. This method comprises either a step of adding, to a reaction mixture, a coordination complex, prepared from the P—C—C—P framework ligand and the transition metal compound, or a step of adding, to a reactor, the P—C—C—P framework ligand and the transition metal compound, so as to produce a P—C—C—P framework ligand coordination complex in situ.

Producing the P—C—C—P framework ligand coordination complex in situ means producing the complex in a medium in which a catalytic reaction occurs. In order for the coordination complex to be produced in situ, it is preferable to add the transition metal compound and the P—C—C—P framework ligand such that the ratio of metal: ligand is typically about 0.01:1-100:1, preferably about 0.1:1-10:1, and more preferably 0.5:1-2:1.

The transition metal may be any one selected from the group consisting of chromium, molybdenum, tungsten, titanium, tantalum, vanadium and zirconium. Preferred is chromium.

When the transition metal compound catalyzing ethylene oligomerization according to the present invention is mixed with the P—C—C—P framework ligand and a promoter, it may be a simple inorganic or organic salt, or a coordination or organometallic compound. This compound is preferably chromium or a chromium precursor. The chromium or chromium precursor is preferably selected from the group consisting of chromium (III) acetylacetonate, tris(tetrahydrofuran) trichlorochromium, and chromium (III) 2-ethylhexanoate.

Also, the P—C—C—P framework ligand can be attached to a polymer chain, such that the resulting ligand coordination complex of P—C—C—P framework structure becomes insoluble above room temperature. Moreover, the P—C—C—P framework ligand or the transition metal compound can be bound and fixed to a backbone, such as silica, silica gel, polysiloxane or alumina.

The promoter for use in the inventive method may be any compound, which produces an active catalyst when it is mixed with the P—C—C—P framework ligand and the transition metal compound. The activator may also be used in a mixture. Compounds suitable for use as the activator include organoaluminium compounds, organoboron compounds and organic salts.

Organoaluminum compounds suitable for use as the activator in the catalyst system according to the present invention include compounds, such as $AlR_3$, wherein the R radicals are each independently $C_1$-$C_{12}$ alkyl, oxygen-containing alkyl or halide), and $LiAlH_4$.

Examples of this promoter include trimethylaluminum (TMA), triethylaluminum (TEA), triisobutylaluminum (TIBA), tri-n-octylaluminum, methylaluminum dichloride, ethylaluminum dichloride, dimethylaluminum chloride, diethylaluminum chloride isopropoxide, ethylaluminum sesquichloride, methylaluminum sesquichloride and aluminoxane.

In the art, aluminoxane is widely known to be an oligomeric compound which can be typically prepared by mixing water and an alkylaluminum compound, for example, trimethylaluminum. The produced aluminoxane oligomeric compound may be a linear compound, a cyclic compound, a cage compound, or a mixture thereof.

Suitable organoboron compounds include boroxin, $NaBH_4$, triethylborane, triphenylborane, triphenylborane ammonia complexes, tributylborate, triisopropylborate, tris(pentafluorophenyl)borane, trityl tetra (pentafluorophenyl) borate, dimethylphenylammonium(tetra pentafluorophenyl) borate, diethylphenylammonium(tetra pentafluorophenyl) borate, methyldiphenylammonium(tetra pentafluorophenyl) borate, and ethyldiphenylammonium(tetra pentafluorophenyl)borate. These organoboron compounds may be used in a mixture with the organoaluminum compounds.

Also, among the promoters, aluminoxane may be selected from among alkylaluminoxanes, for example, methylaluminoxane (MAO) and ethylaluminoxane (EAO), as well as modified alkylaluminoxanes, for example, modified methylaluminoxane (MMAO). The modified methyl aluminoxane (Akzo Nobel) contains, in addition to a methyl group, a branched alkyl group such as an isobutyl or n-octyl group.

The promoter is preferably methylaluminoxane (MAO) or ethylaluminoxane (EAO).

The transition metal chromium compound and the aluminoxane may be mixed such that the ratio of aluminum: metal is about 1:1-10,000:1, and preferably about 1:1-1,000:1.

The individual components of the catalyst system disclosed herein may be mixed simultaneously or sequentially in any order in the presence or absence of a solvent to provide an active catalyst. The mixing of the components of the catalyst can be performed at a temperature between −20° C. and 250° C. During the mixing of the catalyst components, the presence of the olefin generally has a protective effect, to thus provide enhanced catalytic performance. More preferably, the mixing of the catalyst components is performed at a temperature ranging from 20° C. to 100° C.

The reaction product disclosed in the present invention, that is, an ethylene oligomer, can be produced using the inventive catalyst system and a catalytic technique in the presence or absence of an inert solvent through a homogeneous liquid reaction, a slurry reaction, in which the catalyst system is not partially or completely dissolved, a two-phase liquid/liquid reaction, a bulky reaction, in which olefin acts as a main medium, or a gaseous reaction.

Thus, the method according to the present invention may be performed in an inert solvent. That is, any inert solvent, which does not react with the catalyst compound or with the activator, may be used. These inert solvents may include saturated aliphatic and unsaturated aliphatic and aromatic hydrocarbons and hydrocarbon halide. Typical solvents include benzene, toluene, xylene, cumene, heptane, cyclohexane, methylcyclohexane, methylcyclopentane, n-hexane, 1-hexene, 1-octene, and the like, but the scope of the present invention is not limited thereto.

The oligomerization reaction according to the present invention can be performed at a temperature of −20 to 250° C., preferably 15 to 130° C., and more preferably 30 to 70° C.

Also, the process according to the present invention can be performed at a pressure ranging from atmospheric pressure to 500 bar, preferably 10 to 70 bar, and more preferably 30-50 bar.

In an embodiment of the present invention, the P—C—C—P framework stereoisomeric ligand coordination complex and reaction conditions are selected such that the yield of 1-hexene from ethylene is more than 50 mass %, and preferably more than 70 mass %. Herein, the yield means the number of grams of 1-hexene formed per 100 g of the formed reaction product.

In another embodiment of the present invention, the P—C—C—P framework stereoisomeric ligand coordination complex and reaction conditions are selected such that the yield of 1-octene from ethylene is more than 50 mass %, and preferably more than 70 mass %. Herein, the yield means the number of grams of 1-octene formed per 100 g of the formed reaction product.

Depending on the P—C—C—P framework ligand and the reaction conditions, the oligomerization process according to the present invention can provide, in addition to 1-hexene or 1-octene, different amounts of 1-butene, 1-hexene, methyl cyclopentane, methylene cyclopentane, propyl cyclopentane and a number of higher oligomers and polyethylenes.

The process according to the present invention can be performed in a plant comprising a reactor of any type. Examples of this reactor include a batch-type reactor, a semi-batch-type reactor, and a continuous reactor, but the scope of the present invention is not limited thereto. The plant may comprise a combination of a reactor, an inlet for introducing olefins and the catalyst system into the reactor, a line for discharging an oligomerization product from the reactor, and at least one separator for separating the oligomerization product, in which the catalyst system may comprise the transition metal compound, the promoter and the P—C—C—P ligand coordination complex, as disclosed herein.

According to the present invention, 1-hexene or 1-octene can be produced with high activity and high selectivity by oligomerizing ethylene using the ethylene oligomerization catalyst system according to the present invention.

MODE FOR INVENTION

Hereinafter, the present invention will be described in further detail with reference to the following preparation examples and examples, but the scope of the present invention is not limited to these examples.

EXAMPLES

Catalyst Preparation Example 1

Preparation of (S,S)-(phenyl)$_2$PCH(methyl)CH(methyl)P(phenyl)$_2$ ligand

Catalyst preparation was carried out as disclosed in B. Bosnich et al, J. Am. Chem. Soc. 99 (19) (1977).

From (2R,3R)-butanediol, (2R,3R)-butanediol di-p-toluenesulfonate was prepared. This preparation process was carried out as disclosed in R. B. Mitra et al, J. Am. Chem. Soc 84 (1962). 100 ml (1.24 mol) of dry pyridine was placed in a 1-liter flask in an ice-water bath and mixed with 100 g (0.525 mol) of chloro-p-toluenesulfonyl, and then 22 ml (0.245 mol) of (2R,3R)-butanediol was slowly added dropwise. After the temperature was elevated to room temperature over 20 minutes, the semi-solid mixture was maintained at room temperature overnight. An excess amount of ice in pieces was added thereto, and the mixture was thoroughly shaken such that no mass was formed. After the powder crystal was slowly separated, it was stirred together with pieces of ice for 2 hours, and broken pieces of ice and 70 ml of concentrated hydrochloric acid solution were added to the mixture with intensive stirring. The extracted slurry was filtered, completely washed with water and dried, thus obtaining 85 g (86.3%) of (2R,3R)-butanediol di-p-toluenesulfonate (m.p.: 62-64° C.).

In a 1-liter three-neck round flask, equipped with a 250-ml addition funnel, a reflux condenser and a nitrogen inlet, 95 g of recrystallized triphenylphosphine and 300 ml of dry tetrahydrofuran were charged. To the solution, 5.0 g of thin lithium pieces were added at 25° C. in a nitrogen atmosphere with stirring. In the solution, LiPPh$_2$ was immediately formed, and the solution was changed to a deep red yellow color while a large amount of heat was generated. The temperature of the solution was elevated slowly to 55° C. over 1 hour, and the solution was stirred for 2 hours while it was cooled again to 25° C. The formed phenyllithium was decomposed by dropwise adding 33 g of distilled and purified t-butylchloride over 45 minutes. The transparent red yellow solution was boiled for 5 minutes, and then cooled again to $-4$° C.

To the cooled solution, 35 g of the above-prepared (2R, 3R)-butanediol di-p-toluenesulfonate, dissolved in 100 ml of dry THF, was added dropwise over 1 hour. The solution was elevated slowly to room temperature, and then stirred for 30 minutes. 30 ml of nitrogen-purged water was added thereto, and THF was removed by distillation under reduced pressure, thus extracting a colorless oil-type product. The product was extracted two times with 150 mL of ether, and then dried with Na$_2$SO$_4$. The ether extract was filtered with a solution of 15 g of nickel perchlorate hexahydrate in 50 ml of ethanol in a nitrogen atmosphere. Na$_2$SO$_4$ remaining in the filter was thoroughly washed with ether, and then the ether solution was added to the nickel solution. The red brown oil-type product, which had yellow crystals, was [Ni((S,S)-chiraphos)$_2$](ClO$_4$)$_2$. The oil crystal mixture was added to 15 g of sodium thiocyanate (NaNCS), dissolved in 50 ml of hot ethanol, and the solution was intensively stirred for a few hours until a uniform yellow-brown solid of [Ni((S,S)-chiraphos)$_2$NCS]NCS was formed. The solid product was completely washed with ethanol, and then washed with ether.

15 g of the nickel complex was suspended in 150 ml of ethanol under nitrogen and heated with stirring. A solution of 4 g of sodium cyanide (NaCN) was rapidly added thereto. The nickel complex was slowly dissolved to produce a clear red solution of [Ni((S,S)-chiraphos)$_2$CN$_3$]$^-$, which was then changed to a turbid beige-colored solution. The hot solution was stirred until a yellow slurry formed. The slurry solution was cooled, and the solid was washed two times with 25 ml of water and rapidly cooled with ice-cooled ethanol. The impurity-containing beige-color solid was dried at 25° C., added to 125 ml of boiling anhydrous ethanol, and then filtered through frit. The frit filtration was performed at room temperature for 12 hours and as a result, the filtrate was completely removed, leaving only a colorless glossy solid. The solid was recrystallized from 60 ml of anhydrous ethanol, thus obtaining 5.5 g of completely colorless pure (S,S)-(phenyl)$_2$PCH(methyl)CH(methyl)P(phenyl)$_2$.

Example 1

Ethylene tetramerization using Cr(III)(acetylacetonate)$_3$, (S,S)-(phenyl)$_2$PCH(methyl)CH(methyl)P(phenyl)$_2$ and MAO A 300-ml stainless steel reactor was washed with nitrogen in a vacuum, and then 100 ml of cyclohexane was added thereto and MAO (4.0 mmol-Al) was added. Then, the temperature was elevated to 45° C. In a 50 ml Schlenk container in a glove box, 3.5 mg (0.010 mmol) of Cr(III)(acetylacetonate)$_3$ in 10 ml of toluene was mixed with 4.3 mg (0.010 mmol) of (S,S)-(phenyl)$_2$PCH(methyl)CH(methyl)P(phenyl)$_2$, prepared in Catalyst Preparation Example 1. The mixture was stirred at room temperature for 5 minutes, and then added to the reactor. The reactor was charged with ethylene to 30 bar, and the mixture was stirred at a speed of 600 rpm. After 30 minutes, the supply of ethylene into the reactor was stopped, the stirring was stopped to terminate the reaction, and the reactor was cooled to below 10° C.

After excess ethylene in the reactor was discharged, ethanol containing 10 vol % hydrochloric acid was added to the liquid in the reactor. In order to analyze the liquid by GC-FID, nonane, as an internal standard, was added. A small amount of the organic layer sample was dried over anhydrous magnesium sulfate, and then analyzed by GC-FID. The remaining organic layer was filtered to separate solid wax/polymer products. These solid products were dried in an oven at 100° C. overnight and weighed, thus obtaining 1.3 g of polyethylene. GC analysis showed that the total weight of the reaction mixture was 38.2 g. The distribution of the products of this Example is summarized in Table 1 below.

Example 2

Ethylene tetramerization using Cr(III)(acetylacetonate)$_3$, (S,S)-(phenyl)$_2$PCH(methyl)CH(methyl)P(phenyl)$_2$ and MAO A 300-ml stainless steel reactor, which was the same as used in Example 1, was washed with nitrogen in a vacuum, and then 100 ml of cyclohexane was added and MAO (2.0 mmol-Al) was added. Then, the temperature in the reactor was elevated to 45° C. In a 50-ml Schlenk container in a glove box, 0.7 mg (0.002 mmol) of Cr(III)(acetylacetonate)$_3$ in 10 ml of toluene was mixed with 0.86 mg (0.002 mmol) of (S,S)-(phenyl)$_2$PCH(methyl)CH(methyl)P(phenyl)$_2$, prepared in Catalyst Preparation Example 1. The mixture was stirred at room temperature for 5 minutes and then added to the reactor. The reactor was charged with ethylene to 30 bar, and the mixture was stirred at a speed of 600 rpm. After 30 minutes, the supply of ethylene into the reactor was stopped, the stirring was stopped to terminate the reaction, and the reactor was cooled below 10° C.

After excess ethylene in the reactor was discharged, ethanol containing 10 vol % hydrochloric acid was added to the liquid in the reactor. In order to analyze the liquid by GC-FID, nonane, as an internal standard, was added. A small amount of the organic layer sample was dried over anhydrous magnesium sulfate and then analyzed by GC-FID. The remaining organic layer was filtered to separate solid wax/polymer products. These solid products were dried in an oven at 100° C. overnight and weighed. GC analysis showed that the weight of the reaction mixture was 18.0 g. The distribution of the products of this Example is summarized in Table 1 below.

Example 3

Ethylene tetramerization using $CrCl_3$(tetrahydrofuran)$_3$, (S,S)-(phenyl)$_2$PCH(methyl)CH(methyl)P(phenyl)$_2$ and MAO A 300-ml stainless steel reactor, which was the same as used in Example 1, was washed with nitrogen in a vacuum, and then 100 ml of cyclohexane was added and MAO (2.0 mmol-Al) was added. Then, the temperature within the reactor was elevated to 45° C. In a 50-ml Schlenk container in a glove box, 3.75 mg (0.01 mmol) of $CrCl_3$(tetrahydrofuran)$_3$ in 10 ml of toluene was mixed with 4.3 mg (0.01 mmol) of (S,S)-(phenyl)$_2$PCH(methyl)CH(methyl)P(phenyl)$_2$, prepared in Catalyst Preparation Example 1. The mixture was stirred at room temperature for 5 minutes and then added to the reactor. The reactor was charged with ethylene to 30 bar, and the mixture was stirred at a speed of 600 rpm. After 30 minutes, the supply of ethylene into the reactor was stopped, the stirring was stopped to terminate the reaction, and the reactor was cooled to below 10° C.

After excess ethylene in the reactor was discharged, ethanol, containing 10 vol % hydrochloric acid, was added to the liquid in the reactor. In order to analyze the liquid by GC-FID, nonane, as an internal standard, was added. A small amount of the organic layer sample was dried over anhydrous magnesium sulfate, and then analyzed by GC-FID. The remaining organic layer was filtered to separate solid wax/polymer products. These solid products were dried in an oven at 100° C. overnight. GC analysis showed that the weight of the reaction mixture was 30.5 g. The distribution of the products of this Example is summarized in Table 1 below.

Example 4

Ethylene tetramerization using Cr(2-ethylhexanoate)$_3$, (S,S)-(phenyl)$_2$PCH(methyl)CH(methyl)P(phenyl)$_2$ and MAO A 300-ml stainless steel reactor, which was the same as used in Example 1, was washed with nitrogen in a vacuum, and then 100 ml of cyclohexane was added and MAO (2.0 mmol-Al) was added. Then, the temperature in the reactor was elevated to 45° C. In a 50-ml Schlenk container in a glove box, 4.0 mg (0.01 mmol) of Cr(ethylhexanoate)$_3$ in 10 ml of toluene was mixed with 4.3 mg (0.01 mmol) of (S,S)-(phenyl)$_2$PCH(methyl)CH(methyl)P(phenyl)$_2$, prepared in Catalyst Preparation Example 1. The mixture was stirred at room temperature for 5 minutes and then added to the reactor. The reactor was charged with ethylene to 30 bar, and the mixture was stirred at a speed of 600 rpm. After 30 minutes, the supply of ethylene into the reactor was stopped, the stirring was stopped to terminate the reaction, and the reactor was cooled to below 10° C.

After excess ethylene in the reactor was discharged, ethanol, containing 10 vol % hydrochloric acid, was added to the liquid in the reactor. In order to analyze the liquid by GC-FID, nonane, as an internal standard, was added. A small amount of the organic layer sample was dried over anhydrous magnesium sulfate and then analyzed by GC-FID. The remaining organic layer was filtered to separate solid wax/polymer products. These solid products were dried in an oven at 100° C. overnight. GC analysis showed that the weight of the reaction mixture was 30.0 g. The distribution of the products of this Example is summarized in Table 1 below.

Example 5

Ethylene tetramerization using Cr(2-ethylhexanoate)$_3$, (S,S)-(phenyl)$_2$PCH(methyl)CH(methyl)P(phenyl)$_2$ and MAO A 300-ml stainless steel reactor of Example 1 was washed with nitrogen in a vacuum, and then 100 ml of cyclohexane was added and MAO (2.0 mmol-Al) was added. Then, the temperature in the reactor was elevated to 45° C. In a 50-ml Schlenk container in a glove box, 0.8 mg (0.002 mmol) of Cr(ethylhexanoate)$_3$ in 10 ml of toluene was mixed with 0.86 mg (0.002 mmol) of (S,S)-(phenyl)$_2$PCH(methyl)CH(methyl)P(phenyl)$_2$, prepared in Catalyst Preparation Example 1. The mixture was stirred at room temperature for 5 minutes and then added to the reactor. The reactor was charged with ethylene to 30 bar, and the mixture was stirred at a speed of 600 rpm. After 30 minutes, the supply of ethylene into the reactor was stopped, the stirring was stopped, to thus terminate the reaction, and the reactor was cooled to below 10° C.

After excess ethylene in the reactor was discharged, ethanol containing 10 vol % hydrochloric acid was added to the liquid in the reactor. In order to analyze the liquid by GC-FID, nonane, as an internal standard, was added. A small amount of the organic layer sample was dried over anhydrous magnesium sulfate, and then analyzed by GC-FID. The remaining organic layer was filtered to separate solid wax/polymer products. These solid products were dried in an oven at 100° C. overnight. GC analysis showed that the weight of the reaction mixture was 11.2 g. The distribution of the products of this Example is summarized in Table 1 below.

Catalyst Preparation Example 2

Preparation of (R,R)-(phenyl)$_2$PCH(methyl)CH(methyl)P(phenyl)$_2$ ligand

A catalyst was prepared in the same manner as in Catalyst Preparation Example 1, except that (2S,3S)-butanediol was used as the starting reaction material instead of (2R,3R)-butanediol. 5.1 g of completely colorless pure (R,R)-(phenyl)$_2$PCH(methyl)CH(methyl)P(phenyl)$_2$ was obtained.

Example 6

Ethylene tetramerization using Cr(III)(acetylacetonate)$_3$, (R,R)-(phenyl)$_2$PCH(methyl)CH(methyl)P(phenyl)$_2$ and MAO The process of Example 1 was repeated, except that (R,R)-(phenyl)$_2$PCH(methyl)CH(methyl)P(phenyl)$_2$ was used instead of (S,S)-(phenyl)$_2$PCH(methyl)CH(methyl)P(phenyl)$_2$ as the ligand. As a result, the total weight of the reaction products was 43.2 g. The distribution of the products of this Example is summarized in Table 1 below.

Example 7

Ethylene tetramerization using CrCl$_3$(tetrahydrofuran)$_3$, (R,R)-(phenyl)$_2$PCH(methyl)CH(methyl)P(phenyl)$_2$ and MAO The process of Example 3 was repeated, except that (R,R)-(phenyl)$_2$PCH(methyl)CH(methyl)P(phenyl)$_2$ was used as the ligand instead of (S,S)-(phenyl)$_2$PCH(methyl)CH(methyl)P(phenyl)$_2$. As a result, the total weight of the reaction products was 25.3 g. The distribution of the products of this Example is summarized in Table 1 below.

Example 8

Ethylene tetramerization using Cr(2-ethylhexanoate)$_3$, (R,R)-(phenyl)$_2$PCH(methyl)CH(methyl)P(phenyl)$_2$ and MAO The process of Example 4 was repeated, except that (R,R)-(phenyl)$_2$PCH(methyl)CH(methyl)P(phenyl)$_2$ was used as the ligand instead of (S,S)-(phenyl)$_2$PCH(methyl)CH(methyl)P(phenyl)$_2$. As a result, the total weight of the reaction products was 40.9 g. The distribution of the products of this Example is summarized in Table 1 below.

Catalyst Preparation Example 3

Preparation of (S,S)-(4-methoxyphenyl)$_2$P—CH(methyl)CH(methyl)-P(4-methoxyphenyl)$_2$ ligand Catalyst preparation was performed as disclosed in B. Bosnich et al, J. Am. Chem. Soc 99 (19)(1977).
The preparation of (2R,3R)-butanediol di-p-toluenesulfonate from (2R,3R)-butanediol was carried out according to the process of Catalyst Preparation Example 1.
The preparation of tri(4-methoxyphenyl)phosphorus was carried out in the following manner. 91.1 g (3.75 mol) of magnesium pieces were slowly added to 95 mL (0.75 mol) of 4-bromo-anisol in 2 liters of THF. After intensive reaction, the reaction mixture was heated under reflux for 2 hours to obtain a Grignard reagent. The Grignard reagent was added dropwise to a solution of 17.5 mL (0.2 mol) of PCl$_3$ in 2 liters of THF at −78° C. over 2 hours with stirring. After completion of the dropwise addition, the dry ice/acetone bath was removed, and the reaction material was warmed to room temperature. The reaction material was stirred overnight, and the solvent was removed in a vacuum. The phosphine product was used in a subsequent step without being removed.
In a 1-liter three-neck round flask, equipped with a 250-ml addition funnel, a reflux condenser and a nitrogen inlet, 70 g of recrytallized tri(4-methoxyphenyl) phosphine and 300 ml of dry tetrahydrofuran were charged. To the solution, 2.8 g of thin lithium pieces were added at 25° C. under a nitrogen atmosphere with stirring. In the solution, LiP(4-OMe-Ph)$_2$ was immediately formed, and the solution was changed to a deep red yellow color while a large amount of heat was generated. The temperature of the solution was elevated slowly to 55° C. over 1 hour, and the solution was stirred for 2 hours while it was cooled again to 25° C. The formed 4-methoxyphenyllithium was decomposed by dropwise adding 18.5 g of distilled and purified t-butylchloride over 45 minutes. The transparent red yellow solution was boiled for 5 minutes, and then cooled again to −4° C.
To the cooled solution, 19.6 g of the above-prepared (2R,3R)-butanediol di-p-toluenesulfonate, dissolved in 100 ml of dry THF, was added dropwise over 1 hour. The solution was warmed slowly to room temperature, and then stirred for 30 minutes. 30 ml of nitrogen-purged water was added thereto, and THF was removed by distillation under reduced pressure, thus extracting a colorless oil-type product. The product was extracted two times with 150 mL of ether, and then dried with Na$_2$SO$_4$. The ether extract was filtered with a solution of 8.4 g of nickel perchlorate hexahydrate in 50 ml of ethanol in a nitrogen atmosphere. Na$_2$SO$_4$ remaining in the filter was thoroughly washed with ether, and then the ether solution was added to the nickel solution. The red brown oil-type product, which often had yellow crystals, was [Ni((2S,3S)-bis(di-p-methoxyphenyl)phosphorus butane)$_2$](ClO$_4$)$_2$. The oil crystal mixture was added to 8.4 g of sodium thiocyanate (NaNCS) dissolved in 50 ml of hot ethanol, and the solution was intensively stirred for a few hours until a uniform yellow-brown solid of [Ni((2S,3S)-bis(di-p-methoxyphenyl)phosphorusbutane)$_2$NCS]NCS was formed. The solid product was completely washed with ethanol, and then washed with ether.
17 g of the nickel complex was suspended in 150 ml of ethanol under nitrogen and heated with stirring. A solution of 4 g of sodium cyanide (NaCN) was rapidly added thereto. The nickel complex was slowly dissolved to produce a clear red solution of [Ni((2S,3S)-bis(di-p-methoxyphenyl)phosphorusbutane)$_2$CN$_3$]$^-$, which was then changed to a turbid beige-colored solution. The hot solution was stirred until a yellow slurry was formed. The slurry solution was cooled, and the solid was washed two times with 25 ml of water and rapidly cooled with ice-cooled ethanol. The impurity-containing beige-colored solid was dried at 25° C., added to 125 ml of boiling anhydrous ethanol, and then filtered through frit. The frit filtration was performed at room temperature for 12 hours, and as a result, the filtrate was completely removed and only a colorless glossy solid remained. The solid was recrystallized from 60 ml of anhydrous ethanol, thus obtaining 6.2 g of completely colorless pure (S,S)-(4-methoxyphenyl)$_2$PCH(methyl)CH(methyl)P(4-methoxyphenyl)$_2$.

Example 9

Ethylene tetramerization using Cr(III)(acetylacetonate)$_3$, (S,S)-(4-methoxyphenyl)$_2$P—CH(methyl)CH(methyl)-P(4-methoxyphenyl)$_2$ and MAO The process of Example 3 was repeated, except that (S,S)-(4-methoxyphenyl)$_2$P—CH(methyl)CH(methyl)-P(4-methoxyphenyl)$_2$, prepared in Catalyst Preparation Example 3, was used instead of (S,S)-(phenyl)$_2$PCH(methyl)CH(methyl)P(phenyl)$_2$ as the ligand. As a result, the total weight of the reaction products was 22.3 g. The distribution of the products of this Example is summarized in Table 1 below.

Example 10

Ethylene tetramerization using CrCl$_3$(tetrahydrofuran)$_3$, (S,S)-(4-methoxyphenyl)$_2$P—CH(methyl)CH(methyl)-P(4-methoxyphenyl)$_2$ and MAO The process of Example 3 was repeated, except that (S,S)-(4-methoxyphenyl)$_2$P—CH(methyl)CH(methyl)-P(4-methoxyphenyl)$_2$, prepared in Catalyst Preparation Example 3, was used as the ligand instead of (S,S)-(phenyl)$_2$PCH(methyl)CH(methyl)P(phenyl)$_2$. As a result, the total weight of the reaction products was 12.8 g. The distribution of the products of this Example is summarized in Table 1 below.

Example 11

Ethylene tetramerization using Cr(2-ethylhexanoate)$_3$, (S,S)-(4-methoxyphenyl)$_2$P—CH(methyl)CH(methyl)-P(4-methoxyphenyl)$_2$ and MAO The process of Example 4 was repeated, except that (S,S)-(4-methoxyphenyl)$_2$P—CH(methyl)CH(methyl)-P(4-methoxyphenyl)$_2$, prepared in Catalyst Preparation Example 3, was used as the ligand instead of (S,S)-(phenyl)$_2$PCH(methyl)CH(methyl)P(phenyl)$_2$. As a result, the total weight of the reaction products was 24.1 g. The distribution of the products of this Example is summarized in Table 1 below.

Catalyst Preparation Example 4

Preparation of (R,R)-(4-methoxyphenyl)$_2$P—CH(methyl)CH(methyl)-P(4-methoxyphenyl)$_2$ ligand The process of Catalyst Preparation Example 3 was repeated, except that (2S,3S)-butanediol was used as the starting material instead of (2R,3R)-butanediol. 6.2 g of completely colorless pure (R,R)-(4-methoxyphenyl)$_2$P—CH(methyl)CH(methyl)-P(4-methoxyphenyl)$_2$ was obtained.

Example 12

Ethylene tetramerization using Cr(III)(acetylacetonate)$_3$, (R,R)-(4-methoxyphenyl)$_2$P—CH(methyl)CH(methyl)-P(4-methoxyphenyl)$_2$ and MAO The process of Example 9 was repeated, except that (R,R)-(4-methoxyphenyl)$_2$P—CH(methyl)CH(methyl)-P(4-methoxyphenyl)$_2$, prepared in Catalyst Preparation Example 4, was used as the ligand instead of (S,S)-(4-methoxyphenyl)$_2$P—CH(methyl)CH(methyl)-P(4-methoxyphenyl)$_2$. As a result, the total weight of the reaction products was 25.7 g. The distribution of the products of this Example is summarized in Table 1 below.

Example 13

Ethylene tetramerization using CrCl$_3$(tetrahydrofuran)$_3$, (R,R)-(4-methoxyphenyl)$_2$P—CH(methyl)CH(methyl)-P(4-methoxyphenyl)$_2$ and MAO The process of Example 10 was repeated, except that (R,R)-(4-methoxyphenyl)$_2$P—CH(methyl)CH(methyl)-P(4-methoxyphenyl)$_2$, prepared in Catalyst Preparation Example 4, was used as the ligand instead of (S,S)-(4-methoxyphenyl)$_2$P—CH(methyl)CH(methyl)-P(4-methoxyphenyl)$_2$. As a result, the total weight of the reaction products was 10.3 g. The distribution of the products of this Example is summarized in Table 1 below.

Example 14

Ethylene tetramerization using Cr(2-ethylhexanoate)$_3$, (R,R)-(4-methoxyphenyl)$_2$P—CH(methyl)CH(methyl)-P(4-methoxyphenyl)$_2$ and MAO The process of Example 11 was repeated, except that (R,R)-(4-methoxyphenyl)$_2$P—CH(methyl)CH(methyl)-P(4-methoxyphenyl)$_2$, prepared in Catalyst Preparation Example 4, was used as the ligand instead of (S,S)-(4-methoxyphenyl)$_2$P—CH(methyl)CH(methyl)-P(4-methoxyphenyl)$_2$. As a result, the total weight of the reaction products was 27.5 g. The distribution of the products of this Example is summarized in Table 1 below.

Catalyst Preparation Example 5

Preparation of (S,S)-(2-methoxyphenyl)$_2$PCH(methyl)CH(methyl)P(2-methoxyphenyl)$_2$ ligand Catalyst preparation was performed as disclosed in B. Bosnich et al, J. Am. Chem. Soc 99 (19)(1977).

From (2R,3R)-butanediol, (2R,3R)-butanediol di-p-toluenesulfonate was prepared. This preparation process was carried out as disclosed in R. B. Mitra et al, J. Am. Chem. Soc 84 (1962). 100 ml (1.24 mol) of dry pyridine was placed in a 1-liter flask in an ice-water bath and mixed with 100 g (0.525 mol) of chloro-p-toluenesulfonyl, and then 22 ml (0.245 mol) of (2R,3R)-butanediol was slowly added dropwise. After the temperature of the solution was elevated to room temperature over 20 minutes, the semi-solid mixture was maintained at room temperature overnight. An excess number of pieces of ice were added thereto, and the mixture was thoroughly shaken such that no mass formed. After the powder crystal was slowly separated, it was stirred together with pieces of ice for 2 hours, and broken pieces of ice and 70 ml of concentrated hydrochloric acid solution were added to the mixture with intensive stirring. The extracted slurry was filtered, completely washed with water and dried, thus obtaining 85 g (86.3%) of (2R,3R)-butanediol di-p-toluenesulfonate (m.p.: 62-64 r).

The preparation of tri(2-methoxyphenyl)phosphorus was carried out in the following manner. 91.1 g (3.75 mol) of magnesium pieces were slowly added to 95 mL (0.75 mol) of 2-bromo-anisol in 2 liters of THF. After intensive reaction, the reaction mixture was heated under reflux for 2 hours to obtain a Grignard reagent. The Grignard reagent was added dropwise to a solution of 17.5 mL (0.2 mol) of PCl$_3$ in 2 liters of THF at −78° C. over 2 hours with stirring. After completion of the dropwise addition, the dry ice/acetone bath was removed, and the reaction material was warmed to room temperature. The reaction material was stirred overnight, and the solvent was removed in a vacuum. The phosphine product was used in a subsequent step without removal.

In a 1-liter three-neck round flask, equipped with a 250-ml addition funnel, a reflux condenser and a nitrogen inlet, 70 g of recrytallized tri(2-methoxyphenol) and 300 ml of dry tetrahydrofuran were charged. To the solution, 2.8 g of thin lithium pieces were added at 25 r under a nitrogen atmosphere with stirring. In the solution, LiP(4-OMe-Ph)$_2$ was immediately formed, and the solution was changed to a deep red yellow color while a large amount of heat was generated. The temperature of the solution was elevated slowly to 55° C. over 1 hour, and the solution was stirred for 2 hours while it was cooled again to 25° C. The formed 2-methoxyphenyllithium was decomposed by dropwise adding 18.5 g of distilled and purified t-butylchloride over 45 minutes. The transparent red yellow solution was boiled for 5 minutes, and then cooled again to −4° C.

To the cooled solution, 19.6 g of the above-prepared (2R,3R)-butanediol di-p-toluenesulfonate, dissolved in 100 ml of dry THF, was added dropwise over 1 hour. The solution was elevated slowly to room temperature, and then stirred for 30 minutes. 30 ml of nitrogen-purged water was added thereto, and THF was removed by distillation under reduced pressure, thus extracting a colorless oil-type product. The product was extracted two times with 150 mL of ether, and then dried with Na$_2$SO$_4$. The ether extract was filtered with a solution of 8.4 g of nickel perchlorate hexahydrate in 50 ml of ethanol in a nitrogen atmosphere. Na$_2$SO$_4$ remaining in the filter was thoroughly washed with ether, and then the ether solution was added to the nickel solution. The red brown oil-type product, which often had yellow crystals, was [Ni((2S,3S)-bis(di-p-methoxyphenyl)phosphorus butane)$_2$](ClO$_4$)$_2$. The oil crystal mixture was added to 8.4 g of sodium thiocyanate (NaNCS), dissolved in 50 ml of hot ethanol, and the solution was intensively stirred for a few hours until a uniform yellow-brown solid of [Ni((2S,3S)-bis(di-p-methoxyphenyl)phosphorusbutane)$_2$NCS]NCS was formed. The solid product was completely washed with ethanol, and was then washed with ether.

17 g of the nickel complex was suspended in 150 ml of ethanol under nitrogen and heated with stirring. A solution of 4 g of sodium cyanide (NaCN) was rapidly added thereto. The nickel complex was slowly dissolved to produce a clear red solution of [Ni((2S,3S)-bis(di-p-methoxyphenyl)phosphorusbutane)$_2$CN$_3$]$^-$, which then changed to a turbid beige-colored solution. The hot solution was stirred until a yellow slurry was formed. The slurry solution was cooled, and the solid was washed two times with 25 ml of water and rapidly cooled with ice-cooled ethanol. The impurity-containing beige-colored solid was dried at 25° C., added to 125 ml of boiling anhydrous ethanol, and then filtered through frit. The frit filtration was performed at room temperature for 12 hours, and as a result, the filtrate was completely removed, leaving only a colorless glossy solid. The solid was recrystallized from 60 ml of anhydrous ethanol, thus obtaining 6.8 g of completely colorless pure (S,S)-(4-methoxyphenyl)$_2$PCH(methyl)CH(methyl)P(2-methoxyphenyl)$_2$.

Example 15

Ethylene trimerization using Cr(III)(acetylacetonate)$_3$, (S,S)-(2-methoxyphenyl)$_2$P—CH(methyl)CH(methyl)-P(2-methoxyphenyl)$_2$ and MAO The process of Example 1 was repeated, except that (S,S)-(2-methoxyphenyl)$_2$P—CH(methyl)CH(methyl)-P(2-methoxyphenyl)$_2$, prepared in Catalyst Preparation Example 5, was used as the ligand instead of (S,S)-(phenyl)$_2$PCH(methyl)CH(methyl)P(phenyl)$_2$. As a result, the total weight of the obtained reaction products was 5.6 g. The distribution of the products of this Example is summarized in Table 1 below.

Example 16

Ethylene trimerization using CrCl$_3$(tetrahydrofuran)$_3$, (S,S)-(2-methoxyphenyl)$_2$P—CH(methyl)CH(methyl)-P(2-methoxyphenyl)$_2$ and MAO The process of Example 3 was repeated, except that (S,S)-(2-methoxyphenyl)$_2$P—CH(methyl)CH(methyl)-P(2-methoxyphenyl)$_2$, prepared in Catalyst Preparation Example 5, was used as the ligand instead of (S,S)-(phenyl)$_2$PCH(methyl)CH(methyl)P(phenyl)$_2$. As a result, the total weight of the obtained reaction products was 3.4 g. The distribution of the products of this Example is summarized in Table 1 below.

Example 17

Ethylene trimerization using Cr(2-ethylhexanoate)$_3$, (S,S)-(2-methoxyphenyl)$_2$P—CH(methyl)CH(methyl)-P(2-methoxyphenyl)$_2$ and MAO The process of Example 4 was repeated, except that (S,S)-(2-methoxyphenyl)$_2$P—CH(methyl)CH(methyl)-P(2-methoxyphenyl)$_2$, prepared in Catalyst Preparation Example 5, was used as the ligand instead of (S,S)-(phenyl)$_2$PCH(methyl)CH(methyl)P(phenyl)$_2$. As a result, the total weight of the obtained reaction products was 4.0 g. The distribution of the products of this Example is summarized in Table 1 below.

Catalyst Preparation Example 6

Preparation of (R,R)-(2-methoxyphenyl)$_2$P—CH(methyl)CH(methyl)-P(2-methoxyphenyl)$_2$ ligand The process of Catalyst Preparation Example 5 was repeated, except that (2S,3S)-butanediol was used as the starting reaction material instead of (2R,3R)-butanediol. 5.3 g of completely colorless pure (R,R)-(2-methoxyphenyl)$_2$P—CH(methyl)CH(methyl)-P(2-methoxyphenyl)$_2$ was obtained.

Example 18

Ethylene trimerization using Cr(III)(acetylacetonate)$_3$, (R,R)-(2-methoxyphenyl)$_2$P—CH(methyl)CH(methyl)-P(2-methoxyphenyl)$_2$ and MAO The process of Example 15 was repeated, except that (R,R)-(2-methoxyphenyl)$_2$P—CH(methyl)CH(methyl)-P(2-methoxyphenyl)$_2$, prepared in Catalyst Preparation Example 6, was used as the ligand instead of (S,S)-(2-methoxyphenyl)$_2$P—CH(methyl)CH(methyl)-P(2-methoxyphenyl)$_2$. As a result, the total weight of the obtained reaction products was 6.7 g. The distribution of the products of this Example is summarized in Table 1 below.

Example 19

Ethylene trimerization using CrCl$_3$(tetrahydrofuran)$_3$, (R,R)-(2-methoxyphenyl)$_2$P—CH(methyl)CH(methyl)-P(2-methoxyphenyl)$_2$ and MAO The process of Example 16 was repeated, except that (R,R)-(2-methoxyphenyl)$_2$P—CH(methyl)CH(methyl)-P(2-methoxyphenyl)$_2$, prepared in Catalyst Preparation Example 6, was used as the ligand instead of (S,S)-(2-methoxyphenyl)$_2$P—CH(methyl)CH(methyl)-P(2-methoxyphenyl)$_2$. As a result, the total weight of the obtained reaction products was 2.8 g. The distribution of the products of this Example is summarized in Table 1 below.

Example 20

Ethylene trimerization using Cr(2-ethylhexanoate)$_3$, (R,R)-(2-methoxyphenyl)$_2$P—CH(methyl)CH(methyl)-P(2-methoxyphenyl)$_2$ and MAO The process of Example 17 was repeated, except that (R,R)-(2-methoxyphenyl)$_2$P—CH(methyl)CH(methyl)-P(2-methoxyphenyl)$_2$, prepared in Catalyst Preparation Example 6, was used as the ligand instead of (S,S)-(2-methoxyphenyl)$_2$P—CH(methyl)CH(methyl)-P(2-methoxyphenyl)$_2$. As a result, the total weight of the obtained reaction products was 3.4 g. The distribution of the products of this Example is summarized in Table 1 below.

Catalyst Preparation Example 7

Preparation of (S,S)-(2-ethylphenyl)$_2$P—CH(methyl)CH(methyl)-P(2-ethylphenyl)$_2$ ligand The process of Catalyst Preparation Example 5 was repeated, except that 2-benzyl bromide was used to prepare tri(2-ethylphenyl)phosphorus. 5.7 g of completely colorless pure (S,S)-(2-ethylphenyl)$_2$P—CH(methyl)CH(methyl)-P(2-ethylphenyl)$_2$ was obtained.

Example 21

Ethylene trimerization using Cr(III)(acetylacetonate)$_3$, (S,S)-(2-ethylphenyl)$_2$P—CH(methyl)CH(methyl)-P(2-ethylphenyl)$_2$ and MAO The process of Example 1 was repeated, except that (S,S)-(2-ethylphenyl)$_2$P—CH(methyl)CH(methyl)-P(2-ethylphenyl)$_2$, prepared in Catalyst Preparation Example 7, was used as the ligand instead of (S,S)-(phenyl)$_2$PCH(methyl)CH(methyl)P(methyl)$_2$. As a result, the total weight of the obtained reaction products was 4.4 g. The distribution of the products of this Example is summarized in Table 1 below.

Example 22

Ethylene trimerization using CrCl$_3$(tetrahydrofuran)$_3$, (S,S)-(2-ethylphenyl)$_2$P—CH(methyl)CH(methyl)-P(2-ethylphenyl)$_2$ and MAO The process of Example 3 was repeated, except that (S,S)-(2-ethylphenyl)$_2$P—CH(methyl)CH(methyl)-P(2-ethylphenyl)$_2$, prepared in Catalyst Preparation Example 7, was used as the ligand instead of (S,S)-(phenyl)$_2$PCH(methyl)CH(methyl)P(methyl)$_2$. As a result, the total weight of the obtained reaction products was 1.8 g. The distribution of the products of this Example is summarized in Table 1 below.

Example 23

Ethylene trimerization using Cr(2-ethylhexanoate)$_3$, (S,S)-(2-ethylphenyl)$_2$P—CH(methyl)CH(methyl)-P(2-ethylphenyl)$_2$ and MAO The process of Example 4 was repeated, except that (S,S)-(2-ethylphenyl)$_2$P—CH(methyl)CH(methyl)-P(2-ethylphenyl)$_2$, prepared in Catalyst Preparation Example 7, was used as the ligand instead of (S,S)-(phenyl)$_2$PCH(methyl)CH(methyl)P(methyl)$_2$. As a result, the total weight of the obtained reaction products was 2.6 g. The distribution of the products of this Example is summarized in Table 1 below.

Catalyst Preparation Example 8

Preparation of (R,R)-(2-ethylphenyl)$_2$P—CH(methyl)CH(methyl)-P(2-ethylphenyl)$_2$ ligand The process of Catalyst Preparation Example 5 was repeated, except that (2S,3S)-butanediol was used as the starting reaction material instead of (2R,3R)-butanediol, and 2-nezyl bromide was used to prepare tri(ethylphenyl)phosphorus. 4.6 g of completely colorless pure (R,R)-(2-ethylphenyl)$_2$P—CH(methyl)CH(methyl)-P(2-ethylphenyl)$_2$ was obtained.

Example 24

Ethylene trimerization using Cr(III)(acetylacetonate)$_3$, (R,R)-(2-ethylphenyl)$_2$P—CH(methyl)CH(methyl)-P(2-ethylphenyl)$_2$ and MAO The process of Example 21 was repeated, except that (R,R)-(2-ethylphenyl)$_2$P—CH(methyl)CH(methyl)-P(2-ethylphenyl)$_2$, prepared in Catalyst Preparation Example 8, was used as the ligand instead of (S,S)-(2-ethylphenyl)$_2$P—CH(methyl)CH(methyl)-P(2-ethylphenyl)$_2$. As a result, the total weight of the obtained reaction products was 5.3 g. The distribution of the products of this Example is summarized in Table 1 below.

Example 25

Ethylene trimerization using CrCl$_3$(tetrahydrofuran)$_3$, (R,R)-(2-ethylphenyl)$_2$P—CH(methyl)CH(methyl)-P(2-ethylphenyl)$_2$ and MAO The process of Example 22 was repeated, except that (R,R)-(2-ethylphenyl)$_2$P—CH(methyl)CH(methyl)-P(2-ethylphenyl)$_2$, prepared in Catalyst Preparation Example 8, was used as the ligand instead of (S,S)-(2-ethylphenyl)$_2$P—CH(methyl)CH(methyl)-P(2-ethylphenyl)$_2$. As a result, the total weight of the obtained reaction products was 2.0 g. The distribution of the products of this Example is summarized in Table 1 below.

Example 26

Ethylene Trimerization using Cr(2-ethylhexanoate)$_3$, (R,R)-(2-ethylphenyl)$_2$P—CH(methyl)CH(methyl)-P(2-ethylphenyl)$_2$ and MAO The process of Example 23 was repeated, except that (R,R)-(2-ethylphenyl)$_2$P—CH(methyl)CH(methyl)-P(2-ethylphenyl)$_2$, prepared in Catalyst Preparation Example 8, was used as the ligand instead of (S,S)-(2-ethylphenyl)$_2$P—CH(methyl)CH(methyl)-P(2-ethylphenyl)$_2$. As a result, the total weight of the obtained reaction products was 2.3 g. The distribution of the products of this Example is summarized in Table 1 below.

Catalyst Preparation Example 9

Preparation of (S,S)-(phenyl)$_2$P—CH(phenyl)CH(phenyl)-P(phenyl)$_2$ ligand

The process of Catalyst Preparation Example 1 was repeated, except that (1R,2R)-1,2-diphenylethanediol was used as the starting material. 3.3 of completely colorless pure (1S,2S)-(phenyl)$_2$P—CH(phenyl)CH(phenyl)-P(2-phenyl)$_2$ was obtained.

Example 27

Ethylene tetramerization using Cr(III)(acetylacetonate)$_3$, (S,S)-(phenyl)$_2$P—CH(phenyl)CH(phenyl)-P(phenyl)$_2$ and MAO The process of Example 1 was repeated, except that (S,S)-(phenyl)$_2$P—CH(phenyl)CH(phenyl)-P(phenyl)$_2$, prepared in Catalyst Preparation Example 9, was used as the ligand instead of (S,S)-(phenyl)$_2$PCH(methyl)CH(methyl)P(phenyl)$_2$. As a result, the total weight of the obtained reaction products was 15.7 g. The distribution of the products of this Example is summarized in Table 1 below.

Example 28

Ethylene tetramerization using CrCl$_3$(tetrahydrofuran)$_3$, (S,S)-(phenyl)$_2$P—CH(phenyl)CH(phenyl)-P(phenyl)$_2$ and MAO The process of Example 3 was repeated, except that (S,S)-(phenyl)$_2$P—CH(phenyl)CH(phenyl)-P(phenyl)$_2$, prepared in Catalyst Preparation Example 9, was used as the ligand instead of (S,S)-(phenyl)$_2$PCH(methyl)CH(methyl)P(phenyl)$_2$. As a result, the total weight of the obtained reaction products was 10.1 g. The distribution of the products of this Example is summarized in Table 1 below.

Example 29

Ethylene tetramerization using Cr(2-ethylhexanoate)$_3$, (S,S)-(phenyl)$_2$P—CH(phenyl)CH(phenyl)-P(phenyl)$_2$ and MAO The process of Example 4 was repeated, except that (S,S)-(phenyl)$_2$P—CH(phenyl)CH(phenyl)-P(phenyl)$_2$, prepared in Catalyst Preparation Example 3, was used as the ligand instead of (S,S)-(phenyl)$_2$PCH(methyl)CH(methyl)P(phenyl)$_2$. As a result, the total weight of the obtained reaction products was 21.5 g. The distribution of the products of this Example is summarized in Table 1 below.

Catalyst Preparation Example 10

Preparation of (R,R)-(phenyl)$_2$P—CH(phenyl)CH(phenyl)-P(phenyl)$_2$ ligand

The process of Catalyst Preparation Example 1 was repeated, except that (1S,2S)-1,2-diphenylethanediol was used as the starting material. 1.5 g of completely colorless pure (1R,2R)-(phenyl)$_2$P—CH(phenyl)CH(phenyl)-P(2-phenyl)$_2$ was obtained.

Example 30

Ethylene trimerization using Cr(III)(acetylacetonate)$_3$, (R,R)-(phenyl)$_2$P—CH(phenyl)CH(phenyl)-P(phenyl)$_2$ and MAO The process of Example 27 was repeated, except that (R,R)-(phenyl)$_2$P—CH(phenyl)CH(phenyl)-P(phenyl)$_2$, prepared in Catalyst Preparation Example 10, was used as the ligand instead of (S,S)-(phenyl)$_2$P—CH(phenyl)CH(phenyl)-P(phenyl)$_2$. As a result, the total weight of the obtained reaction products was 16.3 g. The distribution of the products of this Example is summarized in Table 1 below.

Example 31

Ethylene trimerization using CrCl$_3$(tetrahydrofuran)$_3$, (R,R)-(phenyl)$_2$P—-CH(phenyl)CH(phenyl)-P(phenyl)$_2$ and MAO The process of Example 28 was repeated, except that (R,R)-(phenyl)$_2$P—CH(phenyl)CH(phenyl)-P(phenyl)$_2$, prepared in Catalyst Preparation Example 10, was used as the ligand instead of (S,S)-(phenyl)$_2$P—CH(phenyl)CH(phenyl)-P(phenyl)$_2$. As a result, the total weight of the obtained reaction products was 9.2 g. The distribution of the products of this Example is summarized in Table 1 below.

Example 32

Ethylene trimerization using Cr(2-ethylhexanoate)$_3$, (R,R)-(phenyl)$_2$P—CH(phenyl)CH(phenyl)-P(phenyl)$_2$ and MAO The process of Example 29 was repeated, except that (R,R)-(phenyl)$_2$P—CH(phenyl)CH(phenyl)-P(phenyl)$_2$, prepared in Catalyst Preparation Example 10, was used as the ligand instead of (S,S)-(phenyl)$_2$P—CH(phenyl)CH(phenyl)-P(phenyl)$_2$. As a result, the total weight of the obtained reaction products was 6.5 g. The distribution of the products of this Example is summarized in Table 1 below.

Catalyst Preparation Example 11

Preparation of (1S,2S)-trans-bis(diphenylphosphino)cyclohexane ligand

The process of Catalyst Preparation Example 1 was repeated, except that (1R,2R)-trans-cyclohexanediol was used as the starting reaction material instead of (2R,3R)-butanediol. 3.6 g of completely colorless pure (1S,2S)-trans-bis(diphenylphosphino)cyclohexane was obtained.

Example 33

Ethylene tetramerization using Cr(III)(acetylacetonate)$_3$, (1S,2S)-trans-bis(diphenylphosphino)cyclohexane and MAO The process of Example 1 was repeated, except that (1S,2S)-trans-bis(diphenylphosphino)cyclohexane, prepared in Catalyst Preparation Example 11, was used as the ligand instead of (S,S)-(phenyl)$_2$PCH(methyl)CH(methyl)P(phenyl)$_2$. As a result, the total weight of the obtained reaction products was 77.5 g. The distribution of the products of this Example is summarized in Table 1 below.

Example 34

Ethylene tetramerization using CrCl$_3$(tetrahydrofuran)$_3$, (1S,2S)-trans-bis(diphenylphosphino)cyclohexane and MAO The process of Example 3 was repeated, except that (1S,2S)-trans-bis(diphenylphosphino)cyclohexane, prepared in Catalyst Preparation Example 11, was used as the ligand instead of (S,S)-(phenyl)$_2$PCH(methyl)CH(methyl)P(phenyl)$_2$. As a result, the total weight of the obtained reaction products was 52.3 g. The distribution of the products of this Example is summarized in Table 1 below.

Example 35

Ethylene tetramerization using Cr(2-ethylhexanoate)$_3$, (1S,2S)-trans-bis(diphenylphosphino)cyclohexane and MAO The process of Example 4 was repeated, except that (1S,2S)-trans-bis(diphenylphosphino)cyclohexane, prepared in Catalyst Preparation Example 11, was used as the ligand instead of (S,S)-(phenyl)$_2$PCH(methyl)CH(methyl)P(phenyl)$_2$. As a result, the total weight of the obtained reaction products was 74.9 g. The distribution of the products of this Example is summarized in Table 2 below.

Catalyst Preparation Example 12

Preparation of (1R,2R)-trans-bis(diphenylphosphino)cyclohexane ligand

The process of Catalyst Preparation Example 1 was repeated, except that (1S,2S)-trans-cyclohexanediol was used instead of (2R,3R)-butanediol as the starting reaction material. 3.9 g of completely colorless pure (1R,2R)-trans-bis(diphenylphosphino)cyclohexane was obtained.

Example 36

Ethylene tetramerization using Cr(III)(acetylacetonate)$_3$, (1R,2R)-trans-bis(diphenylphosphino)cyclohexane and MAO The process of Example 1 was repeated, except that (1R,2R)-trans-bis(diphenylphosphino)cyclohexane, prepared in Catalyst Preparation Example 12, was used as the ligand instead of (S,S)-(phenyl)$_2$PCH(methyl)CH(methyl)P(phenyl)$_2$. As a result, the total weight of the obtained reaction products was 83.5 g. The distribution of the products of this Example is summarized in Table 2 below.

Example 37

Ethylene tetramerization using CrCl$_3$(tetrahydrofuran)$_3$, (1R,2R)-trans-bis(diphenylphosphino)cyclohexane and MAO The process of Example 3 was repeated, except that (1R,2R)-trans-bis(diphenylphosphino)cyclohexane, prepared in Catalyst Preparation Example 12, was used as the ligand instead of (S,S)-(phenyl)$_2$PCH(methyl)CH(methyl)P(phenyl)$_2$. As a result, the total weight of the obtained reaction products was 56.4 g. The distribution of the products of this Example is summarized in Table 2 below.

Example 38

Ethylene tetramerization using Cr(2-ethylhexanoate)$_3$, (1R,2R)-trans-bis(diphenylphosphino)cyclohexane and MAO The process of Example 4 was repeated, except that (1R,2R)-trans-bis(diphenylphosphino)cyclohexane, prepared in Catalyst Preparation Example 12, was used as the ligand instead of (S,S)-(phenyl)$_2$PCH(methyl)CH(methyl)P(phenyl)$_2$. As a result, the total weight of the obtained reaction products was 75.6 g. The distribution of the products of this Example is summarized in Table 2 below.

Catalyst Preparation Example 13

Preparation of (1S,2S)-trans-bis(di(4-methoxyphenyl)phosphino)cyclohexane ligand The process of Catalyst Preparation Example 3 was repeated, except that (1R,2R)-trans-cyclohexanediol was used instead of (2R,3R)-butanediol as the starting reaction material. 3.8 g of completely colorless pure (1S,2S)-trans-bis(di(4-methoxyphenyl)phosphino)cyclohexane was obtained.

Example 39

Ethylene tetramerization using Cr(III)(acetylacetonate)$_3$, (1S,2S)-trans-bis(di(4-methoxyphenyl)phosphino)cyclohexane and MAO The process of Example 1 was repeated, except that (1S,2S)-trans-bis(di(4-methoxyphenyl)phosphino)cyclohexane, prepared in Catalyst Preparation Example 13, was used as the ligand instead of (S,S)-(phenyl)$_2$PCH(methyl)CH(methyl)P(phenyl)$_2$. As a result, the total weight of the obtained reaction products was 124 g. The distribution of the products of this Example is summarized in Table 2 below.

Example 40

Ethylene tetramerization using CrCl$_3$(tetrahydrofuran)$_3$, (1S,2S)-trans-bis(di(4-methoxyphenyl)phosphino)cyclohexane and MAO The process of Example 3 was repeated, except that (1S,2S)-trans-bis(di(4-methoxyphenyl)phosphino)cyclohexane, prepared in Catalyst Preparation Example 13, was used as the ligand instead of (S,S)-(phenyl)$_2$PCH(methyl)CH(methyl)P(phenyl)$_2$. As a result, the total weight of the obtained reaction products was 82.7 g. The distribution of the products of this Example is summarized in Table 2 below.

Example 41

Ethylene tetramerization using Cr(2-ethylhexanoate)$_3$, (1S,2S)-trans-bis(di(4-methoxyphenyl)phosphino)cyclohexane and MAO The process of Example 4 was repeated, except that (1S,2S)-trans-bis(di(4-methoxyphenyl)phosphino)cyclohexane, prepared in Catalyst Preparation Example 13, was used as the ligand instead of (S,S)-(phenyl)$_2$PCH(methyl)CH(methyl)P(phenyl)$_2$. As a result, the total weight of the obtained reaction products was 110.6 g. The distribution of the products of this Example is summarized in Table 2 below.

Catalyst Preparation Example 14

Preparation of (1R,2R)-trans-bis(di(4-methoxyphenyl)phosphino)cyclohexane ligand The process of Catalyst Preparation Example 3 was repeated, except that (1S,2S)-trans-cyclohexanediol was used as the starting reaction material instead of (2R,3R)-butanediol. 3.9 g of completely colorless pure (1R,2R)-trans-bis(di(4-methoxyphenyl)phosphino)cyclohexane was obtained.

Example 42

Ethylene tetramerization using Cr(III)(acetylacetonate)$_3$, (1R,2R)-trans-bis(di(4-methoxyphenyl)phosphino)cyclohexane and MAO The process of Example 1 was repeated, except that (1R,2R)-trans-bis(di(4-methoxyphenyl)phosphino)cyclohexane, prepared in Catalyst Preparation Example 14, was used as the ligand instead of (S,S)-(phenyl)$_2$PCH(methyl)CH(methyl)P (phenyl)$_2$. As a result, the total weight of the obtained reaction products was 123.8 g. The distribution of the products of this Example is summarized in Table 2 below.

Example 43

Ethylene tetramerization using CrCl$_3$(tetrahydrofuran)$_3$, (1R,2R)-trans-bis(di(4-methoxyphenyl)phosphino)cyclohexane and MAO The process of Example 3 was repeated, except that (1R, 2R)-trans-bis(di(4-methoxyphenyl)phosphino)cyclohexane, prepared in Catalyst Preparation Example 14, was used as the ligand instead of (S,S)-(phenyl)$_2$PCH(methyl)CH(methyl)P(phenyl)$_2$. As a result, the total weight of the obtained reaction products was 90.2 g. The distribution of the products of this Example is summarized in Table 2 below.

Example 44

Ethylene tetramerization using Cr(2-ethylhexanoate)$_3$, (1R,2R)-trans-bis(di(4-methoxyphenyl)phosphino)cyclohexane and MAO The process of Example 4 was repeated, except that (1R, 2R)-trans-bis(di(4-methoxyphenyl)phosphino)cyclohexane, prepared in Catalyst Preparation Example 14, was used as the ligand instead of (S,S)-(phenyl)$_2$PCH(methyl)CH(methyl)P(phenyl)$_2$. As a result, the total weight of the obtained reaction products was 134 g. The distribution of the products of this Example is summarized in Table 2 below.

Catalyst Preparation Example 15

Preparation of (S,S)(4-methylphenyl)$_2$P—CH(methyl)CH(methyl)-P(4-methylphenyl)$_2$ ligand The process of Catalyst Preparation Example 3 was repeated, except that 4-tolyl bromide was used to produce tri(4-methylphenyl)phosphorus. 3.9 g of completely colorless pure (S,S)-(4-methylphenyl)$_2$P—CH(methyl)CH(methyl)-P(4-methylphenyl)$_2$ was obtained.

Example 45

Ethylene tetramerization using Cr(III)(acetylacetonate)$_3$, (S,S)-(4-methylphenyl)$_2$P—CH(methyl)CH(methyl)-P(4-methylphenyl)$_2$ and MAO The process of Example 1 was repeated, except that (S,S)-(4-methylphenyl)$_2$P—CH(methyl)CH(methyl)-P(4-methylphenyl)$_2$, prepared in Catalyst Preparation Example 15, was used as the ligand instead of (S,S)-(phenyl)$_2$PCH(methyl)CH(methyl)P(phenyl)$_2$. As a result, the total weight of the obtained reaction products was 55.9 g. The distribution of the products of this Example is summarized in Table 2 below.

Example 46

Ethylene tetramerization using CrCl$_3$(tetrahydrofuran)$_3$, (S,S)-(4-methylphenyl)$_2$P—CH(methyl)CH(methyl)-P(4-methylphenyl)$_2$ and MAO The process of Example 3 was repeated, except that (S,S)-(4-methylphenyl)$_2$P—CH(methyl)CH(methyl)-P(4-methylphenyl)$_2$, prepared in Catalyst Preparation Example 15, was used as the ligand instead of (S,S)-(phenyl)$_2$PCH(methyl)CH(methyl)P(phenyl)$_2$. As a result, the total weight of the obtained reaction products was 24.8 g. The distribution of the products of this Example is summarized in Table 2 below.

Example 47

Ethylene tetramerization using Cr(2-ethylhexanoate)$_3$, (S,S)-(4-methylphenyl)$_2$P—CH(methyl)CH(methyl)-P(4-methylphenyl)$_2$ and MAO The process of Example 4 was repeated, except that (S,S)-(4-methylphenyl)$_2$P—CH(methyl)CH(methyl)-P(4-methylphenyl)$_2$, prepared in Catalyst Preparation Example 15, was used as the ligand instead of (S,S)-(phenyl)$_2$PCH(methyl)CH(methyl)P(phenyl)$_2$. As a result, the total weight of the obtained reaction products was 42.1 g. The distribution of the products of this Example is summarized in Table 2 below.

Catalyst Preparation Example 16

Preparation of (R,R)-(4-methylphenyl)$_2$P—CH(methyl)CH(methyl)-P(4-methylphenyl)$_2$ ligand The process of Catalyst Preparation Example 15 was repeated, except that (2S,3S)-butanediol was used as the starting reaction material instead of (2R,3R)-butanediol. 4.5 g of completely colorless pure (R,R)-(4-methylphenyl)$_2$P—CH(methyl)CH(methyl)-P(4-methylphenyl)$_2$ was obtained.

Example 48

Ethylene tetramerization using Cr(III)(acetylacetonate)$_3$, (R,R)-(4-methylphenyl)$_2$P—CH(methyl)CH(methyl)-P(4-methylphenyl)$_2$ and MAO The process of Example 45 was repeated, except that (R,R)-(4-methylphenyl)$_2$P—CH(methyl)CH(methyl)-P(4-methylphenyl)$_2$, prepared in Catalyst Preparation Example 16, was used as the ligand instead of (S,S)-(4-methylphenyl)$_2$P—CH(methyl)CH(methyl)-P(4-methylphenyl)$_2$. As a result, the total weight of the obtained reaction products was 50.4 g. The distribution of the products of this Example is summarized in Table 2 below.

Example 49

Ethylene tetramerization using CrCl$_3$(tetrahydrofuran)$_3$, (R,R)-(4-methylphenyl)$_2$P—CH(methyl)CH(methyl)-P(4-methylphenyl)$_2$ and MAO The process of Example 46 was repeated, except that (R,R)-(4-methylphenyl)$_2$P—CH(methyl)CH(methyl)-P(4-methylphenyl)$_2$, prepared in Catalyst Preparation Example 16, was used as the ligand instead of (S,S)-(4-methylphenyl)$_2$P—CH(methyl)CH(methyl)-P(4-methylphenyl)$_2$. As a result, the total weight of the obtained reaction products was 22.1 g. The distribution of the products of this Example is summarized in Table 2 below.

Example 50

Ethylene tetramerization using Cr(2-ethylhexanoate)$_3$, (R,R)-(4-methylphenyl)$_2$P—CH(methyl)CH(methyl)-P(4-methylphenyl)$_2$ and MAO The process of Example 47 was repeated, except that (R,R)-(4-methylphenyl)$_2$P—CH(methyl)CH(methyl)-P(4- methylphenyl)$_2$, prepared in Catalyst Preparation Example 16, was used as the ligand instead of (S,S)-(4-methylphenyl)$_2$P—CH(methyl)CH(methyl)-P(4-methylphenyl)$_2$. As a result, the total weight of the obtained reaction products was 46.5 g. The distribution of the products of this Example is summarized in Table 2 below.

Catalyst Preparation Example 17

Preparation of (1S,2S)-trans-bis(di(2-methoxyphenyl)phosphino)cyclohexane ligand The process of Catalyst Preparation Example 5 was repeated, except that (1R,2R)-trans-cyclohexanediol was used as the starting reaction material instead of (2R,3R)-butanediol. 3.3 g of completely colorless pure (1S,2S)-trans-bis(di(2-methoxyphenyl)phosphino)cyclohexane was obtained.

Example 51

Ethylene trimerization using Cr(III)(acetylacetonate)$_3$, (1S,2S)-trans-bis(di(2-methoxyphenyl)phosphino)cyclohexane and MAO The process of Example 1 was repeated, except that (1S,2S)-trans-bis(di(2-methoxyphenyl)phosphino)cyclohexane, prepared in Catalyst Preparation Example 17, was used as the ligand instead of (S,S)-(phenyl)$_2$PCH(methyl)CH(methyl)P(phenyl)$_2$. As a result, the total weight of the obtained reaction products was 63.4 g. The distribution of the products of this Example is summarized in Table 2 below.

Example 52

Ethylene trimerization using CrCl$_3$(tetrahydrofuran)$_3$, (1S,2S)-trans-bis(di(2-methoxyphenyl)phosphino)cyclohexane and MAO The process of Example 3 was repeated, except that (1S,2S)-trans-bis(di(2-methoxyphenyl)phosphino)cyclohexane, prepared in Catalyst Preparation Example 17, was used as the ligand instead of (S,S)-(phenyl)$_2$PCH(methyl)CH(methyl)P(phenyl)$_2$. As a result, the total weight of the obtained reaction products was 26.8 g. The distribution of the products of this Example is summarized in Table 2 below.

Example 53

Ethylene trimerization using Cr(2-ethylhexanoate)$_3$, (1S,2S)-trans-bis(di(2-methoxyphenyl)phosphino)cyclohexane and MAO The process of Example 4 was repeated, except that (1S,2S)-trans-bis(di(2-methoxyphenyl)phosphino)cyclohexane, prepared in Catalyst Preparation Example 17, was used as the ligand instead of (S,S)-(phenyl)$_2$PCH(methyl)CH(methyl)P(phenyl)$_2$. As a result, the total weight of the obtained reaction products was 43.4 g. The distribution of the products of this Example is summarized in Table 2 below.

Catalyst Preparation Example 18

Preparation of (1R,2R)-trans-bis(di(2-methoxyphenyl)phosphino)cyclohexane ligand The process of Catalyst Preparation Example 5 was repeated, except that (1S,2S)-trans-cyclohexanediol was used as the starting reaction material instead of (2R,3R)-butanediol. 2.5 g of completely colorless pure (1R,2R)-trans-bis(di(2-methoxyphenyl)phosphino)cyclohexane was obtained.

Example 54

Ethylene trimerization using Cr(III)(acetylacetonate)$_3$, (1R,2R)-trans-bis(di(2-methoxyphenyl)phosphino)cyclohexane and MAO The process of Example 1 was repeated, except that (1R,2R)-trans-bis(di(2-methoxyphenyl)phosphino)cyclohexane, prepared in Catalyst Preparation Example 18, was used as the ligand instead of (S,S)-(phenyl)$_2$PCH(methyl)CH(methyl)P(phenyl)$_2$. As a result, the total weight of the obtained reaction products was 75.4 g. The distribution of the products of this Example is summarized in Table 2 below.

Example 55

Ethylene trimerization using CrCl$_3$(tetrahydrofuran)$_3$, (1R,2R)-trans-bis(di(2-methoxyphenyl)phosphino)cyclohexane and MAO The process of Example 3 was repeated, except that (1R,2R)-trans-bis(di(2-methoxyphenyl)phosphino)cyclohexane, prepared in Catalyst Preparation Example 18, was used as the ligand instead of (S,S)-(phenyl)$_2$PCH(methyl)CH(methyl)P(phenyl)$_2$. As a result, the total weight of the obtained reaction products was 20.4 g. The distribution of the products of this Example is summarized in Table 2 below.

Example 56

Ethylene trimerization using Cr(2-ethylhexanoate)$_3$, (1R,2R)-trans-bis(di(2-methoxyphenyl)phosphino)cyclohexane and MAO The process of Example 4 was repeated, except that (1R,2R)-trans-bis(di(2-methoxyphenyl)phosphino)cyclohexane, prepared in Catalyst Preparation Example 18, was used as the ligand instead of (S,S)-(phenyl)$_2$PCH(methyl)CH(methyl)P(phenyl)$_2$. As a result, the total weight of the obtained reaction products was 38.2 g. The distribution of the products of this Example is summarized in Table 2 below.

Catalyst Preparation Example 19

Preparation of (1S,2S)-trans-bis(di(2-ethylphenyl)phosphino)cyclohexane ligand

The process of Catalyst Preparation Example 5 was repeated, except that (1R,2R)-trans-cyclohexanediol was used as the starting reaction material instead of (2R,3R)-butanediol, and 2-benzyl bromide was used to prepare tri(2-ethylphenyl)phosphorus. 4.1 g of completely colorless pure (1S,2S)-trans-bis(di(2-ethylphenyl)phosphino)cyclohexane was obtained.

Example 57

Ethylene trimerization using Cr(III)(acetylacetonate)$_3$, (1S,2S)-trans-bis(di(2-erthylphenyl)phosphino)cyclohexane and MAO The process of Example 1 was repeated, except that (1S,2S)-trans-bis(di(2-ethylphenyl)phosphino)cyclohexane, prepared in Catalyst Preparation Example 19, was used as the ligand instead of (S,S)-(phenyl)$_2$PCH(methyl)CH(methyl)P (phenyl)$_2$. As a result, the total weight of the obtained reaction products was 43.2 g. The distribution of the products of this Example is summarized in Table 2 below.

Example 58

Ethylene trimerization using CrCl$_3$(tetrahydrofuran)$_3$, (1S,2S)-trans-bis(di(2-erthylphenyl)phosphino)cyclohexane and MAO The process of Example 3 was repeated, except that (1S,2S)-trans-bis(di(2-ethylphenyl)phosphino)cyclohexane, prepared in Catalyst Preparation Example 19, was used as the ligand instead of (S,S)-(phenyl)$_2$PCH(methyl)CH(methyl)P (phenyl)$_2$. As a result, the total weight of the obtained reaction products was 16.3 g. The distribution of the products of this Example is summarized in Table 2 below.

Example 59

Ethylene trimerization using Cr(2-ethylhexanoate)$_3$, (1S,2S)-trans-bis(di(2-erthylphenyl)phosphino)cyclohexane and MAO The process of Example 4 was repeated, except that (1S,2S)-trans-bis(di(2-ethylphenyl)phosphino)cyclohexane, prepared in Catalyst Preparation Example 19, was used as the ligand instead of (S,S)-(phenyl)$_2$PCH(methyl)CH(methyl)P (phenyl)$_2$. As a result, the total weight of the obtained reaction products was 28.3 g. The distribution of the products of this Example is summarized in Table 2 below.

Catalyst Preparation Example 20

Preparation of (1R,2R)-trans-bis(di(2-ethylphenyl) phosphino)cyclohexane ligand

The process of Catalyst Preparation Example 5 was repeated, except that (1S,2S)-trans-cyclohexanediol was used as the starting reaction material instead of (2R,3R)-butanediol, and 2-bebzyl bromide was used to prepare tri(2-ethylphenyl)phosphorus. 2.9 g of completely colorless pure (1R,2R)-trans-bis(di(2-ethylphenyl)phosphino)cyclohexane was obtained.

Example 60

Ethylene trimerization using Cr(III)(acetylacetonate)$_3$, (1R,2R)-trans-bis(di(2-ethylphenyl)phosphino)cyclohexane and MAO The process of Example 1 was repeated, except that (1R,2R)-trans-bis(di(2-ethylphenyl)phosphino)cyclohexane, prepared in Catalyst Preparation Example 20, was used as the ligand instead of (S,S)-(phenyl)$_2$PCH(methyl)CH(methyl)P (phenyl)$_2$. As a result, the total weight of the obtained reaction products was 50.5 g. The distribution of the products of this Example is summarized in Table 2 below.

Example 61

Ethylene trimerization using CrCl$_3$(tetrahydrofuran)$_3$, (1R,2R)-trans-bis(di(2-ethylphenyl)phosphino)cyclohexane and MAO The process of Example 3 was repeated, except that (1R,2R)-trans-bis(di(2-ethylphenyl)phosphino)cyclohexane, prepared in Catalyst Preparation Example 20, was used as the ligand instead of (S,S)-(phenyl)$_2$PCH(methyl)CH(methyl)P (phenyl)$_2$. As a result, the total weight of the obtained reaction products was 21.3 g. The distribution of the products of this Example is summarized in Table 2 below.

Example 62

Ethylene trimerization using Cr(2-ethylhexanoate)$_3$, (1R,2R)-trans-bis(di(2-ethylphenyl)phosphino)cyclohexane and MAO The process of Example 4 was repeated, except that (1R,2R)-trans-bis(di(2-ethylphenyl)phosphino)cyclohexane, prepared in Catalyst Preparation Example 20, was used as the ligand instead of (S,S)-(phenyl)$_2$PCH(methyl)CH(methyl)P (phenyl)$_2$. As a result, the total weight of the obtained reaction products was 23.4 g. The distribution of the products of this Example is summarized in Table 2 below.

Catalyst Preparation Example 21

Preparation of (S,S)-(2-methylphenyl)$_2$P—CH(methyl)CH(methyl)-P(2-methylphenyl)$_2$ ligand The process of Catalyst Preparation Example 3 was repeated, except that 3-tolyl bromide was used to prepare tri(2-methylphenyl)phosphorus. 3.6 g of completely colorless pure (S,S)-(2-methylphenyl)$_2$P—CH(methyl)CH(methyl)-P(2-methylphenyl)$_2$ was obtained.

Example 63

Ethylene tetramerization using Cr(III)(acetylacetonate)$_3$, (S,S)-(2-methylphenyl)$_2$P—CH(methyl)CH(methyl)-P(2-methylphenyl)$_2$ and MAO The process of Example 1 was repeated, except that (S,S)-(2-methylphenyl)$_2$P—CH(methyl)CH(methyl)-P(2-methylphenyl)$_2$, prepared in Catalyst Preparation Example 21, was used as the ligand instead of (S,S)-(phenyl)$_2$PCH(methyl)CH(methyl)P(phenyl)$_2$. As a result, the total weight of the obtained reaction products was 5.0 g. The distribution of the products of this Example is summarized in Table 2 below.

Example 64

Ethylene tetramerization using CrCl$_3$(tetrahydrofuran)$_3$, (S,S)-(2-methylphenyl)$_2$P—CH(methyl)CH(methyl)-P(2-methylphenyl)$_2$ and MAO The process of Example 3 was repeated, except that (S,S)-(2-methylphenyl)$_2$P—CH(methyl)CH(methyl)-P(2-methylphenyl)$_2$, prepared in Catalyst Preparation Example 21, was used as the ligand instead of (S,S)-(phenyl)$_2$PCH(methyl)CH(methyl)P(phenyl)$_2$. As a result, the total weight of the obtained reaction products was 1.8 g. The distribution of the products of this Example is summarized in Table 2 below.

Example 65

Ethylene tetramerization using Cr(2-ethylhexanoate)$_3$, (S,S)-(2-methylphenyl)$_2$P—CH(methyl)CH(methyl)-P(2-methylphenyl)$_2$ and MAO The process of Example 4 was repeated, except that (S,S)-(2-methylphenyl)$_2$P—CH(methyl)CH(methyl)-P(2-methylphenyl)$_2$, prepared in Catalyst Preparation Example 21, was used as the ligand instead of (S,S)-(phenyl)$_2$PCH(methyl)CH(methyl)P(phenyl)$_2$. As a result, the total weight of the obtained reaction products was 3.2 g. The distribution of the products of this Example is summarized in Table 2 below.

Catalyst Preparation Example 22

Preparation of (R,R)-(2-methylphenyl)$_2$P—CH(methyl)CH(methyl)-P(2-methylphenyl)$_2$ ligand The process of Catalyst Preparation Example 21 was repeated, except that (2S,3S)-butanediol was used as the starting reaction material instead of (2R,3R)-butanediol. 4.0 g of completely colorless (R,R)-(2-methylphenyl)$_2$P—CH(methyl)CH(methyl)-P(2-methylphenyl)$_2$ was obtained.

Example 66

Ethylene tetramerization using Cr(III)(acetylacetonate)$_3$, (R,R)-(2-methylphenyl)$_2$P—CH(methyl)CH(methyl)-P(2-methylphenyl)$_2$ and MAO The process of Example 63 was repeated, except that (R,R)-(2-methylphenyl)$_2$P—CH(methyl)CH(methyl)-P(2-methylphenyl)$_2$, prepared in Catalyst Preparation Example 22, was used as the ligand instead of (S,S)-(2-methylphenyl)$_2$P—CH(methyl)CH(methyl)-P(2-methylphenyl)$_2$. As a result, the total weight of the obtained reaction products was 4.0 g. The distribution of the products of this Example is summarized in Table 2 below.

Example 67

Ethylene tetramerization using CrCl$_3$(tetrahydrofuran)$_3$, (R,R)-(2-methylphenyl)$_2$P—CH(methyl)CH(methyl)-P(2-methylphenyl)$_2$ and MAO The process of Example 64 was repeated, except that (R,R)-(2-methylphenyl)$_2$P—CH(methyl)CH(methyl)-P(2-methylphenyl)$_2$, prepared in Catalyst Preparation Example 22, was used as the ligand instead of (S,S)-(2-methylphenyl)$_2$P—CH(methyl)CH(methyl)-P(2-methylphenyl)$_2$. As a result, the total weight of the obtained reaction products was 2.3 g. The distribution of the products of this Example is summarized in Table 2 below.

Example 68

Ethylene tetramerization using Cr(2-ethylhexanoate)$_3$, (R,R)-(2-methylphenyl)$_2$P—CH(methyl)CH(methyl)-P(2-methylphenyl)$_2$ and MAO The process of Example 65 was repeated, except that (R,R)-(2-methylphenyl)$_2$P—CH(methyl)CH(methyl)-P(2-methylphenyl)$_2$, prepared in Catalyst Preparation Example 22, was used as the ligand instead of (S,S)-(2-methylphenyl)$_2$P—CH(methyl)CH(methyl)-P(2-methylphenyl)$_2$. As a result, the total weight of the obtained reaction products was 2.0 g. The distribution of the products of this Example is summarized in Table 2 below.

Comparative Catalyst Preparation Example 1

Preparation of meso-(phenyl)$_2$PCH(methyl)CH(methyl)P(phenyl)$_2$ ligand

The process of Catalyst Preparation Example 1 was repeated, except that meso-butanediol was used as the starting reaction material instead of (2R,3R)-butanediol. 5.7 g of completely colorless pure meso-(phenyl)$_2$PCH(methyl)CH(methyl)P(phenyl)$_2$ was obtained.

Comparative Example 1

Ethylene tetramerization using Cr(III)(acetylacetonate)$_3$, meso-(phenyl)$_2$PCH(methyl)CH(methyl)P(phenyl)$_2$ ligand and MAO The process of Example 1 was repeated, except that meso-(phenyl)$_2$PCH(methyl)CH(methyl)P(phenyl)$_2$, prepared in Comparative Catalyst Preparation Example 1, was used as the ligand instead of (S,S)-(phenyl)$_2$PCH(methyl)CH(methyl)P(phenyl). As a result, the total weight of the obtained reaction products was 7.3 g. The distribution of the products of this Example is summarized in Table 3 below.

Comparative Example 2

Ethylene tetramerization using CrCl$_3$(tetrahydrofuran)$_3$, meso-(phenyl)$_2$PCH(methyl)CH(methyl)P(phenyl)$_2$ ligand and MAO The process of Example 3 was repeated, except that meso-(phenyl)$_2$PCH(methyl)CH(methyl)P(phenyl)$_2$, prepared in Comparative Catalyst Preparation Example 1, was used as the ligand instead of (S,S)-(phenyl)$_2$PCH(methyl)CH(methyl)P(phenyl). As a result, the total weight of the obtained reaction products was 4.3 g. The distribution of the products of this Example is summarized in Table 3 below.

Comparative Example 3

Cr(2-ethylhexanoate)$_3$, meso-(phenyl)$_2$PCH(methyl)CH(methyl)P(phenyl)$_2$ ligand and MAO The process of Example 4 was repeated, except that meso-(phenyl)$_2$PCH(methyl)CH(methyl)P(phenyl)$_2$, prepared in Comparative Catalyst Preparation Example 1, was used as the ligand instead of (S,S)-(phenyl)$_2$PCH(methyl)CH(methyl)P(phenyl). As a result, the total weight of the obtained reaction products was 6.8 g. The distribution of the products of this Example is summarized in Table 3 below.

Comparative Catalyst Preparation Example 2

Preparation of meso-(4-methoxyphenyl)$_2$PCH(methyl)CH(methyl)P(4-methoxyphenyl)$_2$ ligand The process of Catalyst Preparation Example 3 was repeated, except that meso-butanediol was used as the starting reaction material instead of (2R,3R)-butanediol. 3.3 g of completely colorless meso-(phenyl)$_2$PCH(methyl)CH(methyl)P(phenyl)$_2$ was obtained.

Comparative Example 4

Ethylene tetramerization using Cr(III)(acetylacetonate)$_3$, meso-(4-methoxyphenyl)$_2$PCH(methyl)CH(methyl)P(4-methoxyphenyl)$_2$ and MAO The process of Example 1 was repeated, except that meso-(phenyl)$_2$PCH(methyl)CH(methyl)P(phenyl)$_2$, prepared in Comparative Catalyst Preparation Example 2, was used as the ligand instead of (S,S)-(phenyl)$_2$PCH(methyl)CH(methyl)P(phenyl)$_2$. As a result, the total weight of the obtained reaction products was 2.3 g. The distribution of the products of this Example is summarized in Table 3 below.

Comparative Example 5

Ethylene tetramerization using $CrCl_3(tetrahydrofuran)_3$ meso-(4-methoxyphenyl)$_2$PCH(methyl)CH(methyl)P(4-methoxyphenyl)$_2$ and MAO The process of Example 3 was repeated, except that meso-(phenyl)$_2$PCH(methyl)CH(methyl)P(phenyl)$_2$, prepared in Comparative Catalyst Preparation Example 2, was used as the ligand instead of (S,S)-(phenyl)$_2$PCH(methyl)CH(methyl)P(phenyl)$_2$. As a result, the total weight of the obtained reaction products was 3.5 g. The distribution of the products of this Example is summarized in Table 3 below.

Comparative Example 6

Ethylene tetramerization using Cr(2-ethylhexanoate)$_3$, meso-(4-methoxyphenyl)$_2$PCH(methyl)CH(methyl)P(4-methoxyphenyl)$_2$ and MAO The process of Example 4 was repeated, except that meso-(phenyl)$_2$PCH(methyl)CH(methyl)P(phenyl)$_2$, prepared in Comparative Catalyst Preparation Example 2, was used as the ligand instead of (S,S)-(phenyl)$_2$PCH(methyl)CH(methyl)P(phenyl)$_2$. As a result, the total weight of the obtained reaction products was 3.9 g. The distribution of the products of this Example is summarized in Table 3 below.

Comparative Catalyst Preparation Example 3

Preparation of meso-(2-methoxyphenyl)$_2$PCH(methyl)CH(methyl)P(2-methoxyphenyl)$_2$ ligand The process of Catalyst Preparation Example 5 was repeated, except that meso-butanediol was used as the starting reaction material instead of (2R,3R)-butanediol. 4.5 g of completely colorless pure meso-(2-methoxyphenyl)$_2$PCH(methyl)CH(methyl)P(2-methoxyphenyl)$_2$ was obtained.

Comparative Example 7

Ethylene tetramerization using Cr(III)(acetylacetonate)$_3$, meso-(2-methoxyphenyl)$_2$PCH(methyl)CH(methyl)P(2-methoxyphenyl)$_2$ and MAO The process of Example 1 was repeated, except that meso-(2-methoxyphenyl)$_2$PCH(methyl)CH(methyl)P(2-methoxyphenyl)$_2$, prepared in Comparative Catalyst Preparation Example 3, was used as the ligand instead of (S,S)-(phenyl)$_2$PCH(methyl)CH(methyl)P(phenyl)$_2$. As a result, the total weight of the obtained reaction products was 5.2 g. The distribution of the products of this Example is summarized in Table 3 below.

Comparative Example 8

Ethylene tetramerization using $CrCl_3(tetrahydrofuran)_3$, meso-(2-methoxyphenyl)$_2$PCH(methyl)CH(methyl)P(2-methoxyphenyl)$_2$ and MAO The process of Example 3 was repeated, except that meso-(2-methoxyphenyl)$_2$PCH(methyl)CH(methyl)P(2-methoxyphenyl)$_2$, prepared in Comparative Catalyst Preparation Example 3, was used as the ligand instead of (S,S)-(phenyl)$_2$PCH(methyl)CH(methyl)P(phenyl)$_2$. As a result, the total weight of the obtained reaction products was 6.5 g. The distribution of the products of this Example is summarized in Table 3 below.

Comparative Example 9

Ethylene tetramerization using Cr(2-ethylhexanoate)$_3$, meso-(2-methoxyphenyl)$_2$PCH(methyl)CH(methyl)P(2-methoxyphenyl)$_2$ and MAO The process of Example 4 was repeated, except that meso-(2-methoxyphenyl)$_2$PCH(methyl)CH(methyl)P(2-methoxyphenyl)$_2$, prepared in Comparative Catalyst Preparation Example 3, was used as the ligand instead of (S,S)-(phenyl)$_2$PCH(methyl)CH(methyl)P(phenyl)$_2$. As a result, the total weight of the obtained reaction products was 4.8 g. The distribution of the products of this Example is summarized in Table 3 below.

Comparative Catalyst Preparation Example 4

Preparation of meso-(2-ethylphenyl)$_2$PCH(methyl)CH(methyl)P(2-ethylphenyl)$_2$ ligand The process of Catalyst Preparation Example 5 was repeated, except that meso-butanediol was used as the starting reaction material instead of (2R,3R)-butanediol, and 2-benzyl bromide was used to prepare tri(2-ethylphenyl)phosphorus. 4.4 g of completely colorless pure meso-(2-ethylphenyl)$_2$PCH(methyl)CH(methyl)P(2-ethylphenyl)$_2$ was obtained.

Comparative Example 10

Ethylene tetramerization using Cr(III)(acetylacetonate)$_3$, meso-(2-ethylphenyl)$_2$PCH(methyl)CH(methyl)P(2-ethylphenyl)$_2$ and MAO The process of Example 1 was repeated, except that meso-(2-ethylphenyl)$_2$PCH(methyl)CH(methyl)P(2-ethylphenyl)$_2$, prepared in Comparative Catalyst Preparation Example 4, was used as the ligand instead of (S,S)-(phenyl)$_2$PCH(methyl)CH(methyl)P(phenyl)$_2$. As a result, the total weight of the obtained reaction products was 10.5 g. The distribution of the products of this Example is summarized in Table 3 below.

Comparative Example 11

Ethylene tetramerization using $CrCl_3(tetrahydrofuran)_3$, meso-2-ethylphenyl)$_2$PCH(methyl)CH(methyl)P(2-ethylphenyl)$_2$ and MAO The process of Example 3 was repeated, except that meso-(2-ethylphenyl)$_2$PCH(methyl)CH(methyl)P(2-ethylphenyl)$_2$, prepared in Comparative Catalyst Preparation Example 4, was used as the ligand instead of (S,S)-(phenyl)$_2$PCH(methyl)CH(methyl)P(phenyl)$_2$. As a result, the total weight of the obtained reaction products was 5.3 g. The distribution of the products of this Example is summarized in Table 3 below.

Comparative Example 12

Ethylene tetramerization using Cr(2-ethylhexanoate)$_3$, meso-(2-ethylphenyl)$_2$PCH(methyl)CH(methyl)P(2-ethylphenyl)$_2$ and MAO The process of Example 4 was repeated, except that meso-(2-ethylphenyl)$_2$PCH(methyl)CH(methyl)P(2-ethylphenyl)$_2$, prepared in Comparative Catalyst Preparation Example 4, was used as the ligand instead of (S,S)-(phenyl)$_2$PCH(methyl)CH(methyl)P(phenyl)$_2$. As a result, the total weight of the obtained reaction products was 6.2 g. The distribution of the products of this Example is summarized in Table 3 below.

Comparative Catalyst Preparation Example 5

Preparation of meso-(phenyl)$_2$P—CH(phenyl)CH(phenyl)-P(phenyl)$_2$

The process of Catalyst Preparation Example 1 was repeated, except that (1R,2S)-1,2-diphenylethanediol was used as the starting reaction material. 2.6 g of completely colorless pure meso-(phenyl)$_2$P—CH(methyl)CH(methyl)-P(2-methoxyphenyl)$_2$ was obtained.

Comparative Example 13

Ethylene tetramerization using Cr(III)(acetylacetonate)$_3$, meso-(phenyl)$_2$P—CH(phenyl)CH(phenyl)-P(phenyl)$_2$ and MAO The process of Example 1 was repeated, except that meso-(phenyl)$_2$P—CH(methyl)CH(methyl)-P(2-methoxyphenyl)$_2$, prepared in Comparative Catalyst Preparation Example 5, was used as the ligand instead of (S,S)-(phenyl)$_2$PCH(methyl)CH(methyl)P(phenyl)$_2$. As a result, the total weight of the obtained reaction products was 8.5 g. The distribution of the products of this Example is summarized in Table 3 below.

Comparative Example 14

Ethylene tetramerization using CrCl$_3$(tetrahydrofuran)$_3$, meso-(phenyl)$_2$P—CH(phenyl)CH(phenyl)-P(phenyl)$_2$ and MAO The process of Example 3 was repeated, except that meso-(phenyl)$_2$P—CH(methyl)CH(methyl)-P(2-methoxyphenyl)$_2$, prepared in Comparative Catalyst Preparation Example 5, was used as the ligand instead of (S,S)-(phenyl)$_2$PCH(methyl)CH(methyl)P(phenyl)$_2$. As a result, the total weight of the obtained reaction products was 3.2 g. The distribution of the products of this Example is summarized in Table 3 below.

Comparative Example 15

Ethylene tetramerization using Cr(2-ethylhexanoate)$_3$, meso-(phenyl)$_2$P—CH(phenyl)CH(phenyl)-P(phenyl)$_2$ and MAO The process of Example 4 was repeated, except that meso-(phenyl)$_2$P—CH(methyl)CH(methyl)-P(2-methoxyphenyl)$_2$, prepared in Comparative Catalyst Preparation Example 5, was used as the ligand instead of (S,S)-(phenyl)$_2$PCH(methyl)CH(methyl)P(phenyl)$_2$. As a result, the total weight of the obtained reaction products was 3.8 g. The distribution of the products of this Example is summarized in Table 3 below.

Comparative Catalyst Preparation Example 6

Preparation of cis-1,2-bis(diphenylphosphino)cyclohexane ligand

The process of Catalyst Preparation Example 1 was repeated, except that cis-1,2-cyclohexanediol was used as the starting reaction material. 4.3 g of completely colorless pure cis-1,2-bis(diphenylphosphino)cyclohexane was obtained.

Comparative Example 16

Ethylene tetramerization using Cr(III)(acetylacetonate)$_3$, cis-1,2-bis(diphenylphosphino)cyclohexane ligand and MAO The process of Example 1 was repeated, except that cis-1,2-bis(diphenylphosphino)cyclohexane, prepared in Comparative Catalyst Preparation Example 6, was used as the ligand instead of (S,S)-(phenyl)$_2$PCH(methyl)CH(methyl)P(phenyl)$_2$. As a result, the total weight of the obtained reaction products was 15.4 g. The distribution of the products of this Example is summarized in Table 3 below.

Comparative Example 17

Ethylene tetramerization using CrCl$_3$(tetrahydrofuran)$_3$, cis-1,2-bis(diphenylphosphino)cyclohexane ligand and MAO The process of Example 3 was repeated, except that cis-1,2-bis(diphenylphosphino)cyclohexane, prepared in Comparative Catalyst Preparation Example 6, was used as the ligand instead of (S,S)-(phenyl)$_2$PCH(methyl)CH(methyl)P(phenyl)$_2$. As a result, the total weight of the obtained reaction products was 7 g. The distribution of the products of this Example is summarized in Table 3 below.

Comparative Example 18

Ethylene tetramerization using Cr(2-ethylhexanoate)$_3$, cis-1,2-bis(diphenylphosphino)cyclohexane ligand and MAO The process of Example 4 was repeated, except that cis-1,2-bis(diphenylphosphino)cyclohexane, prepared in Comparative Catalyst Preparation Example 6, was used as the ligand instead of (S,S)-(phenyl)$_2$PCH(methyl)CH(methyl)P(phenyl)$_2$. As a result, the total weight of the obtained reaction products was 10.8 g. The distribution of the products of this Example is summarized in Table 3 below.

Comparative Catalyst Preparation Example 7

Preparation of cis-1,2-bis(di(4-methoxyphenyl)phosphino)cyclohexane ligand

The process of Catalyst Preparation Example 3 was repeated, except that cis-1,2-cyclohexanediol was used as the starting reaction material instead of (2R,3R)-butanediol. 3.0 g of completely colorless pure cis-1,2-bis(di(4-methoxyphenyl)phosphino)cyclohexane was obtained.

Comparative Example 19

Ethylene tetramerization using Cr(III)(acetylacetonate)$_3$, cis-1,2-bis(di(4-methoxyphenyl)phosphino)cyclohexane ligand and MAO The process of Example 1 was repeated, except that cis-1,2-bis(di(4-methoxyphenyl)phosphino)cyclohexane, prepared in Comparative Catalyst Preparation Example 7, was used as the ligand instead of (S,S)-(phenyl)$_2$PCH(methyl)CH(methyl)P(phenyl)$_2$. As a result, the total weight of the obtained reaction products was 3.9 g. The distribution of the products of this Example is summarized in Table 3 below.

Comparative Example 20

Ethylene tetramerization using CrCl$_3$(tetrahydrofuran)$_3$, cis-1,2-bis(di(4-methoxyphenyl)phosphino)cyclohexane ligand and MAO The process of Example 3 was repeated, except that cis-1,2-bis(di(4-methoxyphenyl)phosphino)cyclohexane, prepared in Comparative Catalyst Preparation Example 7, was used as the ligand instead of (S,S)-(phenyl)$_2$PCH(methyl)CH(methyl)P(phenyl)$_2$. As a result, the total weight of the obtained reaction products was 2.4 g. The distribution of the products of this Example is summarized in Table 3 below.

Comparative Example 21

Ethylene tetramerization using Cr(2-ethylhexanoate)$_3$, cis-1,2-bis(di(4-methoxyphenyl)phosphino)cyclohexane ligand and MAO The process of Example 4 was repeated, except that cis-1,2-bis(di(4-methoxyphenyl)phosphino)cyclohexane, prepared in Comparative Catalyst Preparation Example 7, was used as the ligand instead of (S,S)-(phenyl)$_2$PCH(methyl)CH(methyl)P(phenyl)$_2$. As a result, the total weight of the obtained reaction products was 2.8 g. The distribution of the products of this Example is summarized in Table 3 below.

Comparative Catalyst Preparation Example 8

Preparation of cis-1,2-bis(di(2-methoxyphenyl)phosphino)cyclohexane ligand

The process of Catalyst Preparation Example 5 was repeated, except that cis-1,2-cyclohexanediol was used as the starting reaction material instead of (2R,3R)-butanediol. 3.9 g of completely colorless pure cis-1,2-bis(di(2-methoxyphenyl)phosphino)cyclohexane was obtained.

Comparative Example 22

Ethylene tetramerization using Cr(III)(acetylacetonate)$_3$, cis-1,2-bis(di(2-methoxyphenyl)phosphino)cyclohexane and MAO The process of Example 1 was repeated, except that cis-1,2-bis(di(2-methoxyphenyl)phosphino)cyclohexane, prepared in Comparative Catalyst Preparation Example 8, was used as the ligand instead of (S,S)-(phenyl)$_2$PCH(methyl)CH(methyl)P(phenyl)$_2$. As a result, the total weight of the obtained reaction products was 7.1 g. The distribution of the products of this Example is summarized in Table 3 below.

Comparative Example 23

Ethylene tetramerization using CrCl$_3$(tetrahydrofuran)$_3$, cis-1,2-bis(di(2-methoxyphenyl)phosphino)cyclohexane and MAO The process of Example 3 was repeated, except that cis-1,2-bis(di(2-methoxyphenyl)phosphino)cyclohexane, prepared in Comparative Catalyst Preparation Example 8, was used as the ligand instead of (S,S)-(phenyl)$_2$PCH(methyl)CH(methyl)P(phenyl)$_2$. As a result, the total weight of the obtained reaction products was 2.9 g. The distribution of the products of this Example is summarized in Table 3 below.

Comparative Example 24

Ethylene tetramerization using Cr(2-ethylhexanoate)$_3$, cis-1,2-bis(di(2-methoxyphenyl)phosphino)cyclohexane and MAO The process of Example 4 was repeated, except that cis-1,2-bis(di(2-methoxyphenyl)phosphino)cyclohexane, prepared in Comparative Catalyst Preparation Example 8, was used as the ligand instead of (S,S)-(phenyl)$_2$PCH(methyl)CH(methyl)P(phenyl)$_2$. As a result, the total weight of the obtained reaction products was 4.7 g. The distribution of the products of this Example is summarized in Table 3 below.

Comparative Catalyst Preparation Example 9

Preparation of cis-1,2-bis(di(2-ethylphenyl)phosphino)cyclohexane ligand

The process of Catalyst Preparation Example 5 was repeated, except that cis-1,2-cyclohexanediol was used as the starting reaction material instead of (2R,3R)-butanediol, and 2-benzyl bromide was used to prepare tri(2-ethylphenyl)phosphorus. 3.0 g of completely colorless pure cis-1,2-bis(di(2-ethylphenyl)phosphino)cyclohexane was obtained.

Comparative Example 25

Ethylene tetramerization using Cr(III)(acetylacetonate)$_3$, cis-1,2-bis(di(2-ethylphenyl)phosphino)cyclohexane ligand and MAO The process of Example 1 was repeated, except that cis-1,2-bis(di(2-ethylphenyl)phosphino)cyclohexane, prepared in Comparative Catalyst Preparation Example 9, was used as the ligand instead of (S,S)-(phenyl)$_2$PCH(methyl)CH(methyl)P(phenyl)$_2$. As a result, the total weight of the obtained reaction products was 7.9 g. The distribution of the products of this Example is summarized in Table 3 below.

Comparative Example 26

Ethylene tetramerization using CrCl$_3$(tetrahydrofuran)$_3$, cis-1,2-bis(di(2-ethylphenyl)phosphino)cyclohexane ligand and MAO The process of Example 3 was repeated, except that cis-1,2-bis(di(2-ethylphenyl)phosphino)cyclohexane, prepared in Comparative Catalyst Preparation Example 9, was used as the ligand instead of (S,S)-(phenyl)$_2$PCH(methyl)CH(methyl)P (phenyl)$_2$. As a result, the total weight of the obtained reaction products was 6.3 g. The distribution of the products of this Example is summarized in Table 3 below.

Comparative Example 27

Ethylene tetramerization using Cr(2-ethylhexanoate)$_3$, cis-1,2-bis(di(2-ethylphenyl)phosphino)cyclohexane ligand and MAO The process of Example 4 was repeated, except that cis-1,2-bis(di(2-ethylphenyl)phosphino)cyclohexane, prepared in Comparative Catalyst Preparation Example 9, was used as the ligand instead of (S,S)-(phenyl)$_2$PCH(methyl)CH(methyl)P (phenyl)$_2$. As a result, the total weight of the obtained reaction products was 3.1 g. The distribution of the products of this Example is summarized in Table 3 below.

Comparative Catalyst Preparation Example 10

Preparation of meso-(4-methylphenyl)$_2$PCH(methyl) CH(methyl)P(4-methylphenyl)$_2$ ligand The process of Catalyst Preparation Example 15 was repeated, except that meso-butanediol was used as the starting reaction material instead of (2R,3R)-butanediol. 4.5 g of completely colorless pure meso-(4-methylphenyl)$_2$PCH(methyl)CH(methyl)P(4-methylphenyl)$_2$ was obtained.

Comparative Example 28

Ethylene tetramerization using Cr(III)(acetylacetonate)$_3$, meso-(4-methylphenyl)$_2$PCH(methyl)CH(methyl)P(4-methylphenyl)$_2$ and MAO The process of Example 1 was repeated, except that meso-(4-methylphenyl)$_2$PCH(methyl)CH(methyl)P(4-methylphenyl)$_2$, prepared in Comparative Catalyst Preparation Example 10, was used as the ligand instead of (S,S)-(phenyl)$_2$PCH (methyl)CH(methyl)P(phenyl)$_2$. As a result, the total weight of the obtained reaction products was 12.3 g. The distribution of the products of this Example is summarized in Table 3 below.

Comparative Example 29

Ethylene tetramerization using CrCl$_3$(tetrahydrofuran)$_3$, meso-(4-methylphenyl)$_2$PCH(methyl)CH(methyl)P(4-methylphenyl)$_2$ and MAO The process of Example 3 was repeated, except that meso-(4-methylphenyl)$_2$PCH(methyl)CH(methyl)P(4-methylphenyl)$_2$, prepared in Comparative Catalyst Preparation Example 10, was used as the ligand instead of (S,S)-(phenyl)$_2$PCH (methyl)CH(methyl)P(phenyl)$_2$. As a result, the total weight of the obtained reaction products was 4.6 g. The distribution of the products of this Example is summarized in Table 3 below.

Comparative Example 30

Ethylene tetramerization using Cr(2-ethylhexanoate)$_3$, meso-(4-methylphenyl)$_2$PCH(methyl)CH(methyl)P(4-methylphenyl)$_2$ and MAO The process of Example 4 was repeated, except that meso-(4-methylphenyl)$_2$PCH(methyl)CH(methyl)P(4-methylphenyl)$_2$, prepared in Comparative Catalyst Preparation Example 10, was used as the ligand instead of (S,S)-(phenyl)$_2$PCH (methyl)CH(methyl)P(phenyl)$_2$. As a result, the total weight of the obtained reaction products was 6.3 g. The distribution of the products of this Example is summarized in Table 3 below.

Comparative Catalyst Preparation Example 11

Preparation of meso-(2-methylphenyl)$_2$PCH(methyl) CH(methyl)P(2-methylphenyl)$_2$ ligand The process of Catalyst Preparation Example 21 was repeated, except that meso-butanediol was used as the starting reaction material instead of (2R,3R)-butanediol. 3.6 g of completely colorless pure meso-(2-methylphenyl)$_2$PCH(methyl)CH(methyl)P(2-methylphenyl)$_2$ was obtained.

Comparative Example 31

Ethylene trimerization using Cr(III)(acetylacetonate)$_3$, meso-(2-methylphenyl)$_2$PCH(methyl)CH(methyl)P(2-methylphenyl)$_2$ and MAO The process of Example 1 was repeated, except that meso-(2-methylphenyl)$_2$PCH(methyl)CH(methyl)P(2-methylphenyl)$_2$, prepared in Comparative Catalyst Preparation Example 11, was used as the ligand instead of (S,S)-(phenyl)$_2$PCH (methyl)CH(methyl)P(phenyl)$_2$. As a result, the total weight of the obtained reaction products was 2.5 g. The distribution of the products of this Example is summarized in Table 3 below.

Comparative Example 32

Ethylene trimerization using CrCl$_3$(tetrahydrofuran)$_3$, meso-(2-methylphenyl)$_2$PCH(methyl)CH(methyl)P(2-methylphenyl)$_2$ and MAO The process of Example 3 was repeated, except that meso-(2-methylphenyl)$_2$PCH(methyl)CH(methyl)P(2-methylphenyl)$_2$, prepared in Comparative Catalyst Preparation Example 11, was used as the ligand instead of (S,S)-(phenyl)$_2$PCH (methyl)CH(methyl)P(phenyl)$_2$. As a result, the total weight of the obtained reaction products was 1.5 g. The distribution of the products of this Example is summarized in Table 3 below.

Comparative Example 33

Ethylene trimerization using Cr(2-ethylhexanoate)$_3$, meso-(2-methylphenyl)$_2$PCH(methyl)CH(methyl)P (2-methylphenyl)$_2$ and MAO The process of Example 4 was repeated, except that meso-(2-methylphenyl)$_2$PCH(methyl)CH(methyl)P(2-methylphenyl)$_2$, prepared in Comparative Catalyst Preparation Example 11, was used as the ligand instead of (S,S)-(phenyl)$_2$PCH (methyl)CH(methyl)P(phenyl)$_2$. As a result, the total weight of the obtained reaction products was 1.6 g. The distribution of the products of this Example is summarized in Table 3 below.

Comparative Catalyst Preparation Example 12

Preparation of (phenyl)$_2$PCH$_2$CH$_2$P(phenyl)$_2$ ligand

According to the method disclosed in R. N. Salvatore et al, *Tetrahedron Letters* 44 (2003), the ligand was prepared by allowing diphenylphosphine to react with 2 molar equivalents of dibromoalkyl in the presence of dimethylformamide (DMF) and cesium hydroxide. Specifically, 360 mg (2.14 mmol) of monohydrated cesium hydroxide was added to a suspension of 16.6 ml of anhydrous N,N-dimethylformamide containing 1.0 g of activated molecular sieve powder having a size of 4 Å, and the mixture was stirred in a nitrogen atmosphere. 0.38 ml (2.14 mmol) of dimethylphosphine was added thereto, and the mixture was stirred at room temperature for 1 hour to obtain a deep orange-colored solution. 0.11 ml (1.29 mmol) of 1,2-dibromoethane was added dropwise to the solution, which then turned white. After the mixture solution was allowed to react at room temperature for 36 hours, 60 ml of distilled water was added to the reaction product, which was then extracted three times with 60 ml of DMC. The organic layer was washed three times with distilled water and dried with anhydrous sodium sulfate. Then, the solvent was removed in a vacuum, and the residue was recrystallized in a benzene solvent, thus obtaining 333 mg (78% yield) of air-sensitive white crystal (333 mg, yield 78%).

Comparative Example 34

Ethylene tetramerization using Cr(III)(acetylacetonate)$_3$, (phenyl)$_2$PCH$_2$CH$_2$P(phenyl)$_2$ and MAO The process of Example 1 was repeated, except that (phenyl)$_2$PCH$_2$CH$_2$P(phenyl)$_2$, prepared in Comparative Catalyst Preparation Example 12, was used as the ligand instead of (S,S)-(phenyl)$_2$PCH(methyl)CH(methyl)P(phenyl)$_2$. As a result, the total weight of the obtained reaction products was 5.5 g. The distribution of the products of this Example is summarized in Table 3 below.

Comparative Example 35

Ethylene tetramerization using Cr(III)(acetylacetonate)$_3$, (phenyl)$_2$PCH$_2$CH$_2$P(phenyl)$_2$ and MAO The process of Example 1 was repeated, except that (phenyl)$_2$PCH$_2$CH$_2$P(phenyl)$_2$, prepared in Comparative Catalyst Preparation Example 12, was used as the ligand instead of (S,S)-(phenyl)$_2$PCH(methyl)CH(methyl)P(phenyl)$_2$, and the reaction pressure was 45 bar. As a result, the total weight of the obtained reaction products was 17.9 g. The distribution of the products of this Example is summarized in Table 3 below.

Comparative Catalyst Preparation Example 13

Preparation of (4-methoxyphenyl)$_2$PCH$_2$CH$_2$P(4-methoxyphenyl)$_2$ ligand

The process of Catalyst Preparation Example 3 was repeated, except that ethyleneglycol was used as the starting reaction material instead of (2R,3R)-butanediol. 4.1 g of completely colorless pure (4-methoxyphenyl)$_2$PCH$_2$CH$_2$P(4-methoxyphenyl)$_2$ was obtained.

Comparative Example 36

Ethylene tetramerization using Cr(III)(acetylacetonate)$_3$, (4-methoxyphenyl)$_2$PCH$_2$CH$_2$P(4-methoxyphenyl)$_2$ and MAO The process of Example 1 was repeated, except that (4-methoxyphenyl)$_2$PCH$_2$CH$_2$P(4-methoxyphenyl)$_2$, prepared in Comparative Catalyst Preparation Example 13, was used as the ligand instead of (S,S)-(phenyl)$_2$PCH(methyl)CH(methyl)P(phenyl)$_2$. As a result, the total weight of the obtained reaction products was 6.3 g. The distribution of the products of this Example is summarized in Table 3 below.

Comparative Example 37

Ethylene tetramerization using Cr(III)(acetylacetonate)$_3$, (4-methoxyphenyl)$_2$PCH$_2$CH$_2$P(4-methoxyphenyl)$_2$ and MAO The process of Example 1 was repeated, except that (4-methoxyphenyl)$_2$PCH$_2$CH$_2$P(4-methoxyphenyl)$_2$, prepared in Comparative Catalyst Preparation Example 13, was used as the ligand instead of (S,S)-(phenyl)$_2$PCH(methyl)CH(methyl)P(phenyl)$_2$, and the reaction pressure was 45 bar. As a result, the total weight of the obtained reaction products was 12.9 g. The distribution of the products of this Example is summarized in Table 3 below.

Comparative Catalyst Preparation Example 14

Preparation of (2-methoxyphenyl)$_2$PCH$_2$CH$_2$P(2-methoxyphenyl)$_2$ ligand

The process of Catalyst Preparation Example 5 was repeated, except that ethylene glycol was used as the starting reaction material instead of (2R,3R)-butanediol. 3.5 g of completely colorless pure (2-methoxyphenyl)$_2$PCH$_2$CH$_2$P(2-methoxyphenyl)$_2$ was obtained.

Comparative Example 38

Ethylene tetramerization using Cr(III)(acetylacetonate)$_3$, (2-methoxyphenyl)$_2$PCH$_2$CH$_2$P(2-methoxyphenyl)$_2$ and MAO The process of Example 1 was repeated, except that (2-methoxyphenyl)$_2$PCH$_2$CH$_2$P(2-methoxyphenyl)$_2$, prepared in Comparative Catalyst Preparation Example 14, was used as the ligand instead of (S,S)-(phenyl)$_2$PCH(methyl)CH(methyl)P(phenyl)$_2$. As a result, no reaction product was produced.

Comparative Example 39

Ethylene tetramerization using Cr(III)(acetylacetonate)$_3$, (2-methoxyphenyl)$_2$PCH$_2$CH$_2$P(2-mehtoxyphenyl)$_2$ and MAO The process of Example 1 was repeated, except that (2-methoxyphenyl)$_2$PCH$_2$CH$_2$P(2-methoxyphenyl)$_2$, prepared in Comparative Catalyst Preparation Example 14, was used as the ligand instead of (S,S)-(phenyl)$_2$PCH(methyl)CH(methyl)P(phenyl)$_2$, and the reaction pressure was 45 bar. As a result, no reaction product was produced.

Comparative Catalyst Preparation Example 15

Preparation of (2-ethylphenyl)$_2$PCH$_2$CH$_2$P(2-ethylphenyl)$_2$ ligand

The process of Catalyst Preparation Example 5 was repeated, except that ethylene glycol was used as the starting reaction material instead of (2R,3R)-butanediol, and 2-benzyl bromide was used to prepare tri(2-ethylphenyl)phosphorus. 2.9 g of completely colorless pure (2-ethylphenyl)$_2$PCH$_2$CH$_2$P(2-ethylphenyl)$_2$ was obtained.

Comparative Example 40

Ethylene tetramerization using Cr(III)(acetylacetonate)$_3$, (2-ethylphenyl)$_2$PCH$_2$CH$_2$P(2-ethylphenyl)$_2$ and MAO The process of Example 1 was repeated, except that (2-ethylphenyl)$_2$PCH$_2$CH$_2$P(2-ethylphenyl)$_2$, prepared in Comparative Catalyst Preparation Example 15, was used as the ligand instead of (S,S)-(phenyl)$_2$PCH(methyl)CH(methyl)P(phenyl)$_2$. As a result, no reaction product was produced.

Comparative Example 41

Ethylene tetramerization using Cr(III)(acetylacetonate)$_3$, (2-ethylphenyl)$_2$PCH$_2$CH$_2$P(2-ethylphenyl)$_2$ and MAO The process of Example 1 was repeated, except that (2-ethylphenyl)$_2$PCH$_2$CH$_2$P(2-ethylphenyl)$_2$, prepared in Comparative Catalyst Preparation Example 15, was used as the ligand instead of (S,S)-(phenyl)$_2$PCH(methyl)CH(methyl)P(phenyl)$_2$, and the reaction pressure was 45 bar. As a result, no reaction product was produced.

Comparative Catalyst Preparation Example 16

Preparation of (phenyl)$_2$PCH$_2$P(phenyl)$_2$ ligand

The process of Comparative Catalyst Preparation Example 10 was repeated, except that dibromomethane was used as the reaction material instead of 1,2-dibromoethane. 390 mg of completely colorless pure (phenyl)$_2$PCH$_2$P(phenyl)$_2$ was obtained.

Comparative Example 42

Ethylene tetramerization using Cr(III)(acetylacetonate)$_3$, (phenyl)$_2$PCH$_2$P(phenyl)$_2$ and MAO The process of Example 1 was repeated, except that (phenyl)$_2$PCH$_2$P(phenyl)$_2$, prepared in Comparative Catalyst Preparation Example 16, was used as the ligand instead of (S,S)-(phenyl)$_2$PCH(methyl)CH(methyl)P(phenyl)$_2$. As a result, the total weight of the obtained reaction products was 1.2 g. The distribution of the products of this Example is summarized in Table 4 below.

Comparative Example 43

Ethylene tetramerization using Cr(III)(acetylacetonate)$_3$, (phenyl)$_2$PCH$_2$P(phenyl)$_2$ and MAO The process of Example 1 was repeated, except that (phenyl)$_2$PCH$_2$P(phenyl)$_2$, prepared in Comparative Catalyst Preparation Example 16, was used as the ligand instead of (S,S)-(phenyl)$_2$PCH(methyl)CH(methyl)P(phenyl)$_2$, and the reaction pressure was 45 bar. As a result, the total weight of the obtained reaction products was 1.7 g. The distribution of the products of this Example is summarized in Table 4 below.

Comparative Catalyst Preparation Example 17

Preparation of (4-methoxyphenyl)$_2$PCH$_2$P(4-methoxyphenyl)$_2$ ligand

The process of Catalyst Preparation Example 3 was repeated, except that diiodomethane was used as the starting reaction material instead of (2R,3R)-butanediol. 4.7 g of completely colorless pure (4-methoxyphenyl)$_2$PCH$_2$P(4-methoxyphenyl)$_2$ was obtained.

Comparative Example 44

Ethylene tetramerization using Cr(III)(acetylacetonate)$_3$, (4-methoxyphenyl)$_2$PCH$_2$P(4-methoxyphenyl)$_2$ and MAO The process of Example 1 was repeated, except that (4-methoxyphenyl)$_2$PCH$_2$P(4-methoxyphenyl)$_2$, prepared in Comparative Catalyst Preparation Example 17, was used as the ligand instead of (S,S)-(phenyl)$_2$PCH(methyl)CH(methyl)P(phenyl)$_2$. As a result, no reaction product was produced.

Comparative Example 45

Ethylene tetramerization using Cr(III)(acetylacetonate)$_3$, (4-methoxyphenyl)$_2$PCH$_2$P(4-methoxyphenyl)$_2$ and MAO The process of Example 1 was repeated, except that (4-methoxyphenyl)$_2$PCH$_2$P(4-methoxyphenyl)$_2$, prepared in Comparative Catalyst Preparation Example 17, was used as the ligand instead of (S,S)-(phenyl)$_2$PCH(methyl)CH(methyl)P(phenyl)$_2$, and the reaction pressure was 45 bar. As a result, no reaction product was produced.

Comparative Catalyst Preparation Example 18

Preparation of (2-methoxyphenyl)$_2$PCH$_2$P(2-methoxyphenyl)$_2$ ligand

The process of Catalyst Preparation Example 5 was repeated, except that diiodomethane was used as the starting reaction material instead of (2R,3R)-butanediol. 1.6 g of completely colorless pure (2-methoxyphenyl)$_2$PCH$_2$P(2-methoxyphenyl)$_2$ was obtained.

Comparative Example 46

Ethylene tetramerization using Cr(III)(acetylacetonate)$_3$, (2-methoxyphenyl)$_2$PCH$_2$P(2-methoxyphenyl)$_2$ and MAO The process of Example 1 was repeated, except that (2-methoxyphenyl)$_2$PCH$_2$P(2-methoxyphenyl)$_2$, prepared in Comparative Catalyst Preparation Example 18, was used as the ligand instead of (S,S)-(phenyl)$_2$PCH(methyl)CH(methyl)P(methyl)$_2$. As a result, no reaction product was produced.

Comparative Example 47

Ethylene tetramerization using Cr(III)(acetylacetonate)$_3$, (2-methoxyphenyl)$_2$PCH$_2$P(2-methoxyphenyl)$_2$ and MAO The process of Example 1 was repeated, except that (2-methoxyphenyl)$_2$PCH$_2$P(2-methoxyphenyl)$_2$, prepared in Comparative Catalyst Preparation Example 18, was used as the ligand instead of (S,S)-(phenyl)$_2$PCH(methyl)CH(methyl)P(methyl)$_2$, and the reaction pressure was 45 bar. As a result, no reaction product was produced.

Comparative Catalyst Preparation Example 19

Preparation of (2-ethylphenyl)$_2$PCH$_2$P(2-ethylphenyl)$_2$ ligand

The process of Catalyst Preparation Example 7 was repeated, except that diiodomethane was used as the starting reaction material instead of (2R,3R)-butanediol. 5.5 g of completely colorless pure (2-ethylphenyl)$_2$PCH$_2$P(2-ethylphenyl)$_2$ was obtained.

Comparative Example 48

Ethylene tetramerization using Cr(III)(acetylacetonate)$_3$, (2-ethylphenyl)$_2$PCH$_2$P(2-ethylphenyl)$_2$ and MAO The process of Example 1 was repeated, except that (2-ethylphenyl)$_2$PCH$_2$P(2-ethylphenyl)$_2$, prepared in Comparative Catalyst Preparation Example 19, was used as the ligand instead of (S,S)-(phenyl)$_2$PCH(methyl)CH(methyl)P(phenyl)$_2$. As a result, no reaction product was produced.

Comparative Example 49

Ethylene tetramerization using Cr(III)(acetylacetonate)$_3$, (2-ethylphenyl)$_2$PCH$_2$P(2-ethylphenyl)$_2$ and MAO The process of Example 1 was repeated, except that (2-ethylphenyl)$_2$PCH$_2$P(2-ethylphenyl)$_2$, prepared in Comparative Catalyst Preparation Example 19, was used as the ligand instead of (S,S)-(phenyl)$_2$PCH(methyl)CH(methyl)P(phenyl)$_2$, and the reaction pressure was 45 bar. As a result, no reaction product was produced.

TABLE 1

| | Total amount of products (g) | Activity (kg/g-Cr) | 1-C6 (%) | 1-C8 (%) | Others (%) | Polymers (%) |
|---|---|---|---|---|---|---|
| Example 1 | 38.2 | 73.5 | 18.5 | 67.9 | 10.1 | 3.5 |
| Example 2 | 18.0 | 173.1 | 17.0 | 68.0 | 10.6 | 4.4 |
| Example 3 | 30.5 | 58.7 | 18.5 | 61.5 | 14.8 | 5.1 |
| Example 4 | 35.0 | 67.3 | 13.1 | 72.9 | 11.6 | 2.6 |
| Example 5 | 11.2 | 107.7 | 16.7 | 69.5 | 10.5 | 3.4 |
| Example 6 | 43.2 | 83.1 | 17.6 | 65.8 | 14.2 | 2.4 |
| Example 7 | 25.3 | 48.7 | 18.0 | 60.0 | 16.6 | 5.4 |
| Example 8 | 40.9 | 78.7 | 16.6 | 71.2 | 8.7 | 3.5 |
| Example 9 | 22.3 | 42.9 | 15.0 | 56.5 | 20.3 | 8.2 |

TABLE 1-continued

| | Total amount of products (g) | Activity (kg/g-Cr) | 1-C6 (%) | 1-C8 (%) | Others (%) | Polymers (%) |
|---|---|---|---|---|---|---|
| Example 10 | 12.8 | 24.6 | 14.5 | 50.4 | 20.8 | 14.3 |
| Example 11 | 24.1 | 46.3 | 13.7 | 68.2 | 14.8 | 3.3 |
| Example 12 | 25.7 | 49.4 | 15.0 | 66.5 | 11.2 | 7.3 |
| Example 13 | 10.3 | 19.8 | 14.5 | 48.2 | 21.1 | 16.2 |
| Example 14 | 27.5 | 52.9 | 13.7 | 62.3 | 19.5 | 4.5 |
| Example 15 | 5.6 | 10.8 | — | — | — | 100.0 |
| Example 16 | 3.4 | 6.5 | — | — | — | 100.0 |
| Example 17 | 4.0 | 7.7 | — | — | — | 100.0 |
| Example 18 | 6.7 | 12.9 | — | — | — | 100.0 |
| Example 19 | 2.8 | 5.4 | — | — | — | 100.0 |
| Example 20 | 3.4 | 6.5 | — | — | — | 100.0 |
| Example 21 | 4.4 | 8.5 | — | — | — | 100.0 |
| Example 22 | 1.8 | 3.5 | — | — | — | 100.0 |
| Example 23 | 2.6 | 5.0 | — | — | — | 100.0 |
| Example 24 | 5.3 | 10.2 | — | — | — | 100.0 |
| Example 25 | 2.0 | 3.8 | — | — | — | 100.0 |
| Example 26 | 2.3 | 4.4 | — | — | — | 100.0 |
| Example 27 | 15.7 | 30.2 | 21.0 | 62.1 | 11.3 | 5.6 |
| Example 28 | 10.1 | 19.4 | 25.3 | 56.5 | 12.0 | 6.2 |
| Example 29 | 21.5 | 41.3 | 23.2 | 64.5 | 8.3 | 4.0 |
| Example 30 | 16.3 | 31.3 | 23.2 | 65.6 | 7.7 | 3.4 |
| Example 31 | 9.2 | 17.7 | 30.5 | 52.3 | 11.6 | 5.6 |
| Example 32 | 16.5 | 31.7 | 18.8 | 67.8 | 10.9 | 2.5 |
| Example 33 | 77.5 | 149.0 | 16.6 | 59.6 | 16.7 | 7.1 |
| Example 34 | 52.3 | 100.6 | 28.4 | 48.5 | 14.7 | 8.4 |

TABLE 2

| | Total amount of products (g) | Activity (kg/g-Cr) | 1-C6 (%) | 1-C8 (%) | Others (%) | Polymers (%) |
|---|---|---|---|---|---|---|
| Example 35 | 74.9 | 144.0 | 22.1 | 55.4 | 16.2 | 6.3 |
| Example 36 | 83.5 | 160.6 | 23.4 | 56.1 | 14.0 | 6.6 |
| Example 37 | 56.4 | 108.5 | 25.5 | 53.2 | 12.1 | 9.2 |
| Example 38 | 75.6 | 145.4 | 19.2 | 60.3 | 15.5 | 5.0 |
| Example 39 | 124.0 | 238.5 | 12.2 | 71.8 | 14.2 | 1.8 |
| Example 40 | 82.7 | 159.0 | 13.6 | 66.4 | 17.9 | 2.1 |
| Example 41 | 110.6 | 212.7 | 11.8 | 72.3 | 14.6 | 1.3 |
| Example 42 | 123.8 | 238.1 | 11.2 | 72.5 | 14.2 | 2.1 |
| Example 43 | 90.2 | 173.5 | 12.9 | 64.8 | 20.0 | 2.3 |
| Example 44 | 134.0 | 257.7 | 13.4 | 70.4 | 15.3 | 0.9 |
| Example 45 | 55.9 | 107.5 | 19.3 | 62.8 | 13.5 | 4.4 |
| Example 46 | 24.8 | 47.7 | 23.5 | 55.4 | 15.5 | 5.6 |
| Example 47 | 42.1 | 81.0 | 22.3 | 61.2 | 13.0 | 3.5 |
| Example 48 | 50.4 | 96.9 | 19.8 | 65.4 | 11.6 | 3.2 |
| Example 49 | 22.1 | 42.5 | 23.6 | 54.3 | 14.5 | 7.6 |
| Example 50 | 46.5 | 89.4 | 21.5 | 60.2 | 14.3 | 4.0 |
| Example 51 | 63.4 | 121.9 | 80.2 | 5.6 | 13.0 | 1.2 |
| Example 52 | 26.8 | 51.5 | 83.8 | 4.1 | 11.2 | 0.9 |
| Example 53 | 43.4 | 83.5 | 89.5 | 3.1 | 5.9 | 1.5 |
| Example 54 | 75.4 | 145.0 | 83.4 | 6.5 | 8.6 | 1.0 |
| Example 55 | 20.4 | 39.2 | 82.3 | 7.1 | 9.6 | 1.7 |
| Example 56 | 38.2 | 73.5 | 82.1 | 6.8 | 9.4 | 1.8 |
| Example 57 | 43.2 | 83.1 | 86.3 | 4.4 | 7.5 | 1.5 |
| Example 58 | 16.3 | 31.3 | 90.2 | 3.2 | 5.1 | 1.5 |
| Example 59 | 28.3 | 54.4 | 89.5 | 2.8 | 5.8 | 1.9 |
| Example 60 | 50.5 | 97.1 | 89.2 | 2.6 | 6.2 | 2.0 |
| Example 61 | 21.3 | 41.0 | 88.8 | 4.5 | 5.4 | 1.3 |
| Example 62 | 23.4 | 45.0 | 87.0 | 4.9 | 6.3 | 1.8 |
| Example 63 | 5.0 | 9.6 | — | — | — | 100.0 |
| Example 64 | 1.8 | 3.5 | — | — | — | 100.0 |
| Example 65 | 3.2 | 6.2 | — | — | — | 100.0 |
| Example 66 | 4.0 | 7.7 | — | — | — | 100.0 |
| Example 67 | 2.3 | 4.4 | — | — | — | 100.0 |
| Example 68 | 2.0 | 3.8 | — | — | — | 100.0 |

TABLE 3

| | Total amount of products (g) | Activity (kg/g-Cr) | 1-C6 (%) | 1-C8 (%) | Others (%) | Polymers (%) |
|---|---|---|---|---|---|---|
| Comparative Example 1 | 7.3 | 14.0 | 15.7 | 50.3 | 13.0 | 21.0 |
| Comparative Example 2 | 4.3 | 8.3 | 14.3 | 48.5 | 7.0 | 30.2 |
| Comparative Example 3 | 6.8 | 13.1 | 14.4 | 46.2 | 11.9 | 27.5 |
| Comparative Example 4 | 2.3 | 4.4 | 6.5 | 7.7 | 3.3 | 82.5 |
| Comparative Example 5 | 3.5 | 6.7 | 3.8 | 5.1 | 3.4 | 87.7 |
| Comparative Example 6 | 3.9 | 7.5 | 2.3 | 4.8 | 3.2 | 89.7 |
| Comparative Example 7 | 5.2 | 10.0 | 0.5 | 1.1 | 0.3 | 98.1 |
| Comparative Example 8 | 6.5 | 12.5 | 1.0 | 0.5 | 0.9 | 97.6 |
| Comparative Example 9 | 4.8 | 9.2 | 0.4 | 0.7 | 2.7 | 96.2 |
| Comparative Example 10 | 10.5 | 20.2 | 1.2 | 0.8 | 2.8 | 95.2 |
| Comparative Example 11 | 5.3 | 10.2 | 0.9 | 3.6 | 1.9 | 93.6 |
| Comparative Example 12 | 6.2 | 11.9 | 3.2 | 2.1 | 3.6 | 90.9 |
| Comparative Example 13 | 8.5 | 16.3 | 7.8 | 3.1 | 0.7 | 88.4 |
| Comparative Example 14 | 3.2 | 6.2 | 6.8 | 2.0 | 4.7 | 86.5 |
| Comparative Example 15 | 3.8 | 7.3 | 5.2 | 1.1 | 6.3 | 87.4 |
| Comparative Example 16 | 15.4 | 29.6 | 23.7 | 45.8 | 14.0 | 16.5 |
| Comparative Example 17 | 17.0 | 13.5 | 26.4 | 36.5 | 17.1 | 20.0 |
| Comparative Example 18 | 10.8 | 20.8 | 19.3 | 38.3 | 15.5 | 26.9 |
| Comparative Example 19 | 3.9 | 7.5 | 4.5 | 6.7 | 3.6 | 85.2 |
| Comparative Example 20 | 2.4 | 4.6 | 3.0 | 4.9 | 8.7 | 83.4 |
| Comparative Example 21 | 2.8 | 5.4 | 3.9 | 6.7 | 4.8 | 84.6 |
| Comparative Example 22 | 7.1 | 13.7 | 1.5 | 2.1 | 1.3 | 95.1 |
| Comparative Example 23 | 2.9 | 5.6 | 1.2 | 1.5 | 3.9 | 93.4 |
| Comparative Example 24 | 4.7 | 9.0 | 0.7 | 1.9 | 3.3 | 94.1 |
| Comparative Example 25 | 7.9 | 15.2 | 1.6 | 1.0 | 4.6 | 92.8 |
| Comparative Example 26 | 6.3 | 12.1 | 2.7 | 1.1 | 2.7 | 93.5 |
| Comparative Example 27 | 3.1 | 6.0 | 1.8 | 2.7 | 5.5 | 90.0 |
| Comparative Example 28 | 12.3 | 23.7 | 7.8 | 6.7 | 9.1 | 76.4 |
| Comparative Example 29 | 4.6 | 8.8 | 4.7 | 6.0 | 7.0 | 82.3 |
| Comparative Example 30 | 6.3 | 12.1 | 8.9 | 8.1 | 5.8 | 77.2 |
| Comparative Example 31 | 2.5 | 4.8 | 0.5 | 1.2 | 5.7 | 92.6 |
| Comparative Example 32 | 1.5 | 2.9 | 1.0 | 1.4 | 4.1 | 93.5 |
| Comparative Example 33 | 1.6 | 3.1 | 1.5 | 1.3 | 5.4 | 91.8 |
| Comparative Example 34 | 5.5 | 10.6 | 5.7 | 34.4 | 24.4 | 35.5 |

TABLE 4

| | Total amount of products (g) | Activity (kg/g-Cr) | 1-C6 (%) | 1-C8 (%) | Others (%) | Polymers (%) |
|---|---|---|---|---|---|---|
| Comparative Example 35 | 17.9 | 34.4 | 9.2 | 22.4 | 36.6 | 31.8 |
| Comparative Example 36 | 6.3 | 12.1 | 24.5 | 50.9 | 7.7 | 16.9 |
| Comparative Example 37 | 12.9 | 24.8 | 18.9 | 53.1 | 7.5 | 20.5 |
| Comparative Example 38 | 0.0 | — | — | — | — | — |
| Comparative Example 39 | 0.0 | — | — | — | — | — |
| Comparative Example 40 | 0.0 | — | — | — | — | — |
| Comparative Example 41 | 0.0 | — | — | — | — | — |
| Comparative Example 42 | 1.2 | 2.3 | — | — | — | 100.0 |
| Comparative Example 43 | 1.7 | 3.3 | — | — | — | 100.0 |
| Comparative Example 44 | 0.0 | — | — | — | — | — |
| Comparative Example 45 | 0.0 | — | — | — | — | — |
| Comparative Example 46 | 0.0 | — | — | — | — | — |
| Comparative Example 47 | 0.0 | — | — | — | — | — |
| Comparative Example 48 | 0.0 | — | — | — | — | — |
| Comparative Example 49 | 0.0 | — | — | — | — | — |

The invention claimed is:

1. A method of producing 1-hexene by selectively trimerizing ethylene using a catalyst system comprising a transition metal or transition metal precursor, a promoter and a ligand represented by any one of the following formulas 1 to 4, wherein the promoter is methylaluminoxane (MAO) or ethylaluminoxane (EAO) and the ligand is sterically asymmetric with respect to a plane of symmetry:

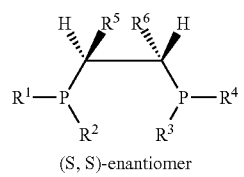

Formula 1

(S, S)-enantiomer

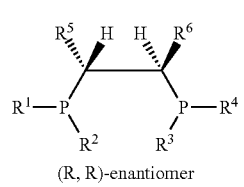

Formula 2

(R, R)-enantiomer

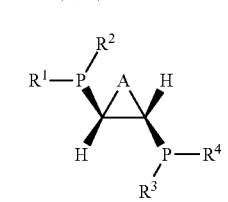

Formula 3

(R, R)-1,2-trans-diphosphoric enantiomer

Formula 4

(S, S)-1,2-trans-diphosphoric enantiomer wherein $R^1$, $R^2$, $R^3$ and $R^4$ are each independently hydrocarbyl, substituted hydrocarbyl, heterohydrocarbyl or substituted heterohydrocarbyl, $R^5$ and $R^6$ are each independently hydrocarbyl or substituted hydrocarbyl, and A is hydrocarbylene, substituted hydrocarbylene, heterohydrocarbylene or substituted heterohydrocarbylene.

2. The method of claim 1, wherein $R^1$, $R^2$, $R^3$ and $R^4$ in the ligand are each independently selected from the group consisting of phenyl, benzyl, naphthyl, anthracenyl, mesityl, xenyl, methyl, ethyl, ethylenyl, propyl, propenyl, propinyl, butyl, cyclohexyl, 4-methylcyclohexyl, 4-ethylcyclohexyl, 4-isopropylcyclohexyl, tolyl, xylyl, 4-methylphenyl, 4-ethylphenyl, 4-isopropylphenyl, 4-t-butylphenyl, 4-methoxyphenyl, 4-isopropoxyphenyl, cumyl, methoxy, ethoxy, phenoxy, tolyloxy, dimethylamino, thiomethyl, trimethylsilyl, dimethylhydrazine, 2-methylcyclohexyl, 2-ethylcyclohexyl, 2-isopropylcyclohexyl, o-methylphenyl, o-ethylphenyl, o-isopropylphenyl, o-t-butylphenyl, o-methoxyphenyl, and o-isopropoxyphenyl.

3. The method of claim 2, wherein R1, R2, R3 and R4 in the ligand are each independently selected from the group consisting of phenyl, tolyl, xenyl, naphthyl, cyclohexyl, 4-methylphenyl, 4-ethylphenyl, 4-isopropylphenyl, 4-t-butylphenyl, 4-methoxyphenyl, 4-isopropoxyphenyl, 2-methylcyclohexyl, 2-ethylcyclohexyl, 2-isopropylcyclohexyl, o-methylphenyl, o-ethylphenyl, o-isopropylphenyl, o-t-butylphenyl, o-methoxyphenyl and o-isopropoxyphenyl.

4. The method of claim 1, wherein R5 and R6 in the ligand are each independently selected from the group consisting of alkyl, substituted alkyl, aryl, substituted aryl, aryloxy, substituted aryloxy, alkoxycarbonyl, carbonyloxy, alkoxy, aminocarbonyl, carbonylamino, dialkylamino, silyl groups, derivatives thereof, and aryl substituted with one or more of these substituents.

5. The method of claim 1, wherein A in the ligand is selected from the group consisting of alkylene, alkoxylene, alkoxycarbonylene, carbonyloxy, aminocarbonylene, carbonylamino, alkylamino, derivatives thereof, and alkylene substituted with one or more of these substituents.

6. The method of claim 1, wherein the ligand is selected from the group consisting of (S,S)- or (R,R)-(phenyl)$_2$P—CH(methyl)CH(methyl)-P(phenyl)$_2$, (S,S)- or (R,R)-(4-methoxyphenyl)$_2$P—CH(methyl)CH(methyl)-P(4-methoxyphenyl)$_2$, (S,S)- or (R,R)-(4-methylphenyl)$_2$P—CH(methyl)CH(methyl)-P(4-methylphenyl)$_2$, (S,S)- or (R,R)-(4-ethylphenyl)$_2$P—CH(methyl)CH(methyl)-P(phenyl)$_2$, (S,S)- or (R,R)-(4-ethylphenyl)$_2$P—CH(ethyl)CH(methyl)-P(4-ethylphenyl)$_2$, (S,S)- or (R,R)-(4-methoxyphenyl)$_2$P—CH(ethyl)CH(methyl)-P(phenyl)$_2$, (S,S)- or (R,R)-(4-ethylphenyl)$_2$P—CH(ethyl)CH(ethyl)-P(4-ethylphenyl)$_2$, (S,S)- or (R,R)-(phenyl)$_2$P—CH(ethyl)CH(ethyl)-P(phenyl)$_2$, (S,S)- or (R,R)-(phenyl)$_2$P—CH(isopropyl)CH(methyl)-P(phenyl)$_2$, (S,S)- or (R,R)-(4-methoxyphenyl)$_2$P—CH(isopropyl)CH(methyl)-P(4-methoxyphenyl)$_2$, (S,S)- or (R,R)-(4-ethylphenyl)$_2$P—CH(isopropyl)CH(methyl)-P(4-ethylphenyl)$_2$, (S,S)- or (R,R)-(phenyl)$_2$P—CH(n-propyl)CH(methyl)-P(phenyl)$_2$, (S,S)- or (R,R)-(4-methoxyphenyl)$_2$P—CH(n-propyl)CH(methyl)-P(4-methoxyphenyl)$_2$, (S,S)- or (R,R)-(4-ethylphenyl)$_2$P—CH(n-propyl)CH(methyl)-P(4-ethylphenyl)$_2$, (S,S)- or (R,R)-(phenyl)$_2$P—CH(isopropyl)CH(ethyl)-P(phenyl)$_2$, (S,S)- or (R,R)-(4-methoxyphenyl)$_2$P—CH(isopropyl)CH(ethyl)-P(4-methoxyphenyl)$_2$, (S,S)- or (R,R)-(4-ethylphenyl)$_2$P—CH(isopropyl)CH(ethyl)-P(4-ethylphenyl)$_2$, (S,S)- or (R,R)-trans-1,2-di-(P(phenyl)$_2$)cyclohexane, (S,S)- or (R,R)-trans-1,2-di-(P(4-methoxyphenyl)$_2$)cyclohexane, (S,S)- or (R,R)-trans-1,2-di-(P(4-ethylphenyl)$_2$)cyclohexane, (S,S)- or (R,R)-trans-1,2-di-(P(phenyl)$_2$)cyclopentane, (S,S)- or (R,R)-trans-1,2-di-(P(4-methoxyphenyl)$_2$)cyclopentane, (S,S)- or (R,R)-1,2-di-(P(4-ethylphenyl)$_2$)cyclopentane, (S,S)- or (R,R)-3,4-di-(P(phenyl)$_2$)pyrrole, (S,S)- or (R,R)-3,4-di-(P(4-methoxyphenyl)$_2$)pyrrole, (S,S)- or (R,R)-trans-3,4-di-(P(4-ethylphenyl)$_2$)pyrrole, (S,S)- or (R,R)-trans-3,4-di-(P(4-ethylphenyl)$_2$)imidazole, (S,S)- or (R,R)-(4-ethylphenyl)$_2$P—CH(dimethylamine)CH(dimethylamine)-P(4-ethylphenyl)$_2$, (S,S)- or (R,R)-(3-methoxyphenyl)$_2$P—CH(methyl)CH(methyl)-P(3-methoxyphenyl)$_2$, ((S,S)- or (R,R)-4-dimethylaminephenyl)$_2$P—CH(methyl)CH(methyl)P(4-dimethylaminephenyl)$_2$, (S,S)- or (R,R)-(4-ethylcyclohexyl)$_2$PCH(methyl)CH(methyl)P(4-ethylcyclohexyl)$_2$, (S,S)- or (R,R)-trans-3,4-di-(P(2-ethylphenyl)$_2$)pyrrole, (S,S)- or (R,R)-trans-3,4-di-(P(2-ethylphenyl)$_2$)imidazole, (S,S)- or (R,R)-(phenyl)$_2$P—CH(phenyl)CH(phenyl)-P(phenyl)$_2$, (1S,2S)- or (1R,2R)-trans-bis(diphenylphosphino)cyclohexane, and (1S,2S)- or (1R,2R)-trans-bis(di(4-methoxyphenyl)phosphino)cyclohexane.

7. The method of claim 1, wherein said transition metal or transition metal precursor is chromium or a chromium precursor.

8. The method of claim 7, wherein said chromium or chromium precursor is selected form the group consisting of chromium (III) acetylacetonate, tris(tetrahydrofuran) trichlorochromium, and chromium (III) 2-ethylhexanoate.

9. A method of producing 1-octene by selectively tetramerizing ethylene using a catalyst system comprising a transition metal or transition metal precursor, a promoter and a ligand represented by any one of the following formulas 1 to 4, wherein the promoter is methylaluminoxane (MAO) or ethylaluminoxane (EAO) and the ligand is sterically asymmetric with respect to a plane of symmetry:

Formula 1

(S, S)-enantiomer

Formula 2

(R, R)-enantiomer

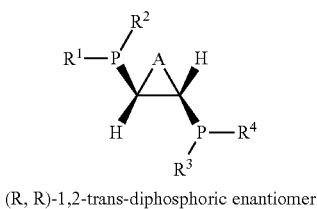

(R, R)-1,2-trans-diphosphoric enantiomer

Formula 3

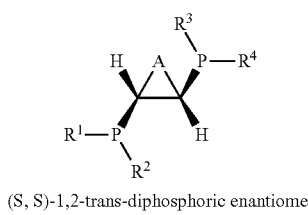

(S, S)-1,2-trans-diphosphoric enantiomer

Formula 4 wherein $R^1$, $R^2$, $R^3$ and $R^4$ are each independently hydrocarbyl, substituted hydrocarbyl, heterohydrocarbyl or substituted heterohydrocarbyl, $R^5$ and $R^6$ are each independently hydrocarbyl or substituted hydrocarbyl, and A is hydrocarbylene, substituted hydrocarbylene, heterohydrocarbylene or substituted heterohydrocarbylene.

10. The method of claim 9, wherein R1, R2, R3 and R4 in the ligand are each independently selected from the group consisting of phenyl, benzyl, naphthyl, anthracenyl, mesityl, xenyl, methyl, ethyl, ethylenyl, propyl, propenyl, propinyl, butyl, cyclohexyl, 4-methylcyclohexyl, 4-ethylcyclohexyl, 4-isopropylcyclohexyl, tolyl, xylyl, 4-methylphenyl, 4-ethylphenyl, 4-isopropylphenyl, 4-t-butylphenyl, 4-methoxyphenyl, 4-isopropoxyphenyl, cumyl, methoxy, ethoxy, phenoxy, tolyloxy, dimethylamino, thiomethyl, trimethylsilyl, dimethylhydrazine, 2-methylcyclohexyl, 2-ethylcyclohexyl, 2-isopropylcyclohexyl, o-methylphenyl, o-ethylphenyl, o-isopropylphenyl, o-t-butylphenyl, o-methoxyphenyl, and o-isopropoxyphenyl.

11. The method of claim 10, wherein R1, R2, R3 and R4 in the ligand are each independently selected from the group consisting of phenyl, tolyl, xenyl, naphthyl, cyclohexyl, 4-methylphenyl, 4-ethylphenyl, 4-isopropylphenyl, 4-t-butylphenyl, 4-methoxyphenyl, 4-isopropoxyphenyl, 2-methylcyclohexyl, 2-ethylcyclohexyl, 2-isopropylcyclohexyl, o-methylphenyl, o-ethylphenyl, o-isopropylphenyl, o-t-butylphenyl, o-methoxyphenyl and o-isopropoxyphenyl.

12. The method of claim 9, wherein R5 and R6 in the ligand are each independently selected from the group consisting of alkyl, substituted alkyl, aryl, substituted aryl, aryloxy, substituted aryloxy, alkoxycarbonyl, carbonyloxy, alkoxy, aminocarbonyl, carbonylamino, dialkylamino, silyl groups, derivatives thereof, and aryl substituted with one or more of these substituents.

13. The method of claim 9, wherein A in the ligand is selected from the group consisting of alkylene, alkoxylene, alkoxycarbonylene, carbonyloxy, aminocarbonylene, carbonylamino, alkylamino, derivatives thereof, and alkylene substituted with one or more of these substituents.

14. The method of claim 9, wherein the ligand is selected from the group consisting of (S,S)- or (R,R)-(phenyl)$_2$P—CH (methyl)CH(methyl)-P(phenyl)$_2$, (S,S)- or (R,R)-(4-methoxyphenyl)$_2$P—CH(methyl)CH(methyl)-P(4-methoxyphenyl)$_2$, (S,S)- or (R,R)-(4-methylphenyl)$_2$P—CH(methyl)CH(methyl)-P(4-methylphenyl)$_2$, (S,S)- or (R,R)-(4-ethylphenyl)$_2$P—CH(methyl)CH(methyl)-P(phenyl)$_2$, (S,S)- or (R,R)-(4-ethylphenyl)$_2$P—CH(ethyl)CH(methyl)-P(4-ethylphenyl)$_2$, (S,S)- or (R,R)-(4-methoxyphenyl)$_2$P—CH(ethyl)CH(methyl)-P(phenyl)$_2$, (S,S)- or (R,R)-(4-ethylphenyl)$_2$P—CH(ethyl)CH(ethyl)-P(4-ethylphenyl)$_2$, (S,S)- or (R,R)-(phenyl)$_2$P—CH(ethyl)CH(ethyl)-P(phenyl)$_2$, (S,S)- or (R,R)-(phenyl)$_2$P—CH(isopropyl)CH(methyl)-P(phenyl)$_2$, (S,S)- or (R,R)-(4-methoxyphenyl)$_2$P—CH(isopropyl)CH(methyl)-P(4-methoxyphenyl)$_2$, (S,S)- or (R,R)-(4-ethylphenyl)$_2$P—CH(isopropyl)CH(methyl)-P(4-ethylphenyl)$_2$, (S,S)- or (R,R)-(phenyl)$_2$P—CH(n-propyl)CH(methyl)-P(phenyl)$_2$, (S,S)- or (R,R)-(4-methoxyphenyl)$_2$P—CH(n-propyl)CH(methyl)-P(4-methoxyphenyl)$_2$, (S,S)- or (R,R)-(4-ethylphenyl)$_2$P—CH(n-propyl)CH(methyl)-P(4-ethylphenyl)$_2$, (S,S)- or (R,R)-(phenyl)$_2$P—CH(isopropyl)CH(ethyl)-P(phenyl)$_2$, (S,S)- or (R,R)-(4-methoxyphenyl)$_2$P—CH(isopropyl)CH(ethyl)-P(4-methoxyphenyl)$_2$, (S,S)- or (R,R)-(4-ethylphenyl)$_2$P—CH(isopropyl)CH(ethyl)-P(4-ethylphenyl)$_2$, (S,S)- or (R,R)-trans-1,2-di-(P(phenyl)$_2$)cyclohexane, (S,S)- or (R,R)-trans-1,2-di-(P(4-methoxyphenyl)$_2$)cyclohexane, (S,S)- or (R,R)-trans-1,2-di-(P(4-ethylphenyl)$_2$)cyclohexane, (S,S)- or (R,R)-trans-1,2-di-(P(phenyl)$_2$)cyclopentane, (S,S)- or (R,R)-trans-1,2-di-(P(4-methoxyphenyl)$_2$)cyclopentane, (S,S)- or (R,R)-1,2-di-(P(4-ethylphenyl)$_2$)cyclopentane, (S,S)- or (R,R)-3,4-di-(P(phenyl)$_2$)pyrrole, (S,S)- or (R,R)-3,4-di-(P(4-methoxyphenyl)$_2$)pyrrole, (S,S)- or (R,R)-trans-3,4-di-(P(4-ethylphenyl)$_2$)pyrrole, (S,S)- or (R,R)-trans-3,4-di-(P(4-ethylphenyl)$_2$)imidazole, (S,S)- or (R,R)-(4-ethylphenyl)$_2$P—CH(dimethylamine)CH(dimethylamine)-P(4-ethylphenyl)$_2$, (S,S)- or (R,R)-(3-methoxyphenyl)$_2$P—CH(methyl)CH(methyl)-P(3-methoxyphenyl)$_2$, ((S,S)- or (R,R)-4-dimethylaminephenyl)$_2$P—CH(methyl)CH(methyl)P(4-dimethylaminephenyl)$_2$, (S,S)- or (R,R)-(4-ethylcyclohexyl)$_2$PCH(methyl)CH(methyl)P(4-ethylcyclohexyl)$_2$, (S,S)- or (R,R)-trans-3,4-di-(P(2-ethylphenyl)$_2$)pyrrole, (S,S)- or (R,R)-trans-3,4-di-(P(2-ethylphenyl)$_2$)imidazole, (S,S)- or (R,R)-(phenyl)$_2$P—CH(phenyl)CH(phenyl)-P(phenyl)$_2$, (1S,2S)- or (1R,2R)-trans-bis(diphenylphosphino)cyclohexane, and (1S,2S)- or (1R,2R)-trans-bis(di(4-methoxyphenyl)phosphino)cyclohexane.

15. The method of claim 9, wherein said transition metal or transition metal precursor is chromium or a chromium precursor.

16. The method of claim 15, wherein said chromium or chromium precursor is selected form the group consisting of chromium (III) acetylacetonate, tris(tetrahydrofuran) trichlorochromium, and chromium (III) 2-ethylhexanoate.

* * * * *